US006635445B1

(12) United States Patent
Igarashi et al.

(10) Patent No.: US 6,635,445 B1
(45) Date of Patent: Oct. 21, 2003

(54) NUCLEIC ACID MOLECULES ENCODING HUMAN LUTEINIZING HORMONE-HUMAN CHORIONIC GONADOTROPIN RECEPTOR PROTEIN AND TRANSFORMANTS THEREOF

(75) Inventors: Masao Igarashi, Gunma (JP); Takashi Minegishi, Gunma (JP); Kazuto Nakamura, Gunma (JP)

(73) Assignee: Takeda Chemical Industries, Ltd., Osaka (JP)

( * ) Notice: Subject to any disclaimer, the term of this patent is extended or adjusted under 35 U.S.C. 154(b) by 0 days.

(21) Appl. No.: 09/461,657

(22) Filed: Dec. 14, 1999

Related U.S. Application Data

(63) Continuation of application No. 07/757,342, filed on Sep. 10, 1991, now Pat. No. 6,218,509.

(30) Foreign Application Priority Data

Sep. 10, 1990 (JP) ........................................ 2-236994
Oct. 20, 1990 (JP) ........................................ 2-280583

(51) Int. Cl.[7] .......................... C12P 21/00; C12N 5/00; C12N 1/00; C07H 21/04; C07K 14/00

(52) U.S. Cl. .................. 435/69.1; 435/70.1; 435/252.3; 435/325; 530/300; 530/350; 536/23.1; 536/23.5

(58) Field of Search .............................. 435/69.1, 70.1, 435/252.3, 320.1, 325; 530/300, 350; 536/23.1, 23.5, 23.51

(56) References Cited

FOREIGN PATENT DOCUMENTS

| EP | 0 108 633 | 7/1983 |
|---|---|---|
| WO | WO 90/13643 | 5/1990 |

OTHER PUBLICATIONS

Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6): 248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Jia et al. Expression of human luteinizing hormone (LH) receptor: interaction with LH and chorionic gonadotropin from human but not equine, rat, and ovine species. Mol Endocrin 5(6): 759–768, 1991.*
A. Frazier et al., *Molecular Endocrinology*, 4:8, pp. 1264–1276 (1990).
H. Loosefelt et al., *Science*, 245, pp. 525–528 (1989).
K.C. McFarland et al., *Science*, 245, pp. 494–499 (1989).
Misrahi et al., *Biochem. Biophys. Res. Comm.*, 166, pp. 394–403 (1990).
Minegish et al., *Biochem. and Biophys. Res. Comm.*, 172, pp. 1049–1054 (1990).
M. Parmentier et al., *Science*, 246, pp. 1620–1622 (1989).
N. Rosemblit et al., *Endocrinology*, 123:5, pp. 2284–2290 (1988).
R. Sprengel et al., *Molecular Endocrinology*, 4, pp. 525–530 (1990).

* cited by examiner

*Primary Examiner*—Elizabeth Kemmerer
*Assistant Examiner*—Bridget E. Bunner
(74) *Attorney, Agent, or Firm*—David G. Conlin; Linda M. Buckley; Diane M. Rees

(57) ABSTRACT

Disclosed are (1) a human luteinizing hormone-human chorionic gonadotropin receptor protein, (2) a DNA comprising a CDNA segment coding for a human luteinizing hormone-human chorionic gonadotropin receptor protein, SEQ ID NO:2 (3) a transformant carrying a DNA comprising a cDNA segment SEQ ID NO:1 coding for a human luteinizing hormone-human chorionic gonadotropin receptor protein, and (4) a method for preparing a human luteinizing hormone-human chorionic gonadotropin receptor protein which comprises cultivating the transformant described in (3), accumulating a protein SEQ ID NO:2 in a culture broth, and collecting the same, whereby the structure and properties of the receptor protein are made clear and the mass production thereof by recombinant technology is pioneered.

7 Claims, 12 Drawing Sheets

| FIG. 1A |
| --- |
| FIG. 1B |
| FIG. 1C |
| FIG. 1D |
| FIG. 1E |

FIG. 1

```
                                                                                 GGCCGCCC   -1

ATGAAGCAGCGGTTCTCGGCGCTGCAGCTCCTGAAGCTGCTGCTGCTGCTCCAGCCGCCGCTGCCACGAGCGCTGCGCGAGGCGCTCTGC   90
MetLysGlnArgPheSerAlaLeuGlnLeuLeuLysLeuLeuLeuLeuLeuGlnProProLeuProArgAlaLeuArgGluAlaLeuCys   30

CCTGAGCCCTGCAACTGCGTGCCCGACGGCGCCCTGCGCTGCCCCGGCCCCACGGCCGGTCTCACTCGACTATCACTTGCCTACCTCCCT  180
ProGluProCysAsnCysValProAspGlyAlaLeuArgCysProGlyProThrAlaGlyLeuThrArgLeuSerLeuAlaTyrLeuPro   60

GTCAAAGTGATCCCATCTCAAGCTTTCAGAGGACTTAATGAGGTCATAAAAATTGAAATCTCTCAGATTGATTCCCTGGAAAGGATAGAA  270
ValLysValIleProSerGlnAlaPheArgGlyLeuAsnGluValIleLysIleGluIleSerGlnIleAspSerLeuGluArgIleGlu   90
```

FIG. 1A

```
GCTAATGCCTTTGACAACCTCCTCAATTTGTCTGAAATACTGATCCAGAACACCAAAAATCTGAGATACATTGAGCCCGGAGCATTTATA   360
AlaAsnAlaPheAspAsnLeuLeuAsnLeuSerGluIleLeuIleGlnAsnThrLysAsnLeuArgTyrIleGluProGlyAlaPheIle   120

AATCTTCCCGGATTAAAATACTTGAGCATCTGTAACACAGGCATCAGAAAGTTTCCAGATGTTACGAAGGTCTTCTCCTCTGAATCAAAT   450
AsnLeuProGlyLeuLysTyrLeuSerIleCysAsnThrGlyIleArgLysPheProAspValThrLysValPheSerSerGluSerAsn   150

TTCATTCTGGAAATTTGTGATAACTTACACATAACCACCATACCAGGAAATGCTTTTCAAGGGATGAATAATGAATCTGTAACACTCAAA   540
PheIleLeuGluIleCysAspAsnLeuHisIleThrThrIleProGlyAsnAlaPheGlnGlyMetAsnAsnGluSerValThrLeuLys   180

CTATATGGAAATGGATTTGAAGAAGTACAAAGTCATGCATTCAATGGGACGACACTGACTTCACTGGAGCTAAAGGAAAACGTACATCTG   630
LeuTyrGlyAsnGlyPheGluGluValGlnSerHisAlaPheAsnGlyThrThrLeuThrSerLeuGluLeuLysGluAsnValHisLeu   210
                                                 679
GAGAAGATGCACAATGGAGCCTTCCGTGGGGCCACAGGGCCGAAAACCTTGGATATTTCTTCCACCAAATTGCAGGCCCTGCCGAGCTAT   720
GluLysMetHisAsnGlyAlaPheArgGlyAlaThrGlyProLysThrLeuAspIleSerSerThrLysLeuGlnAlaLeuProSerTyr   240
                                                 227
GGCCTAGAGTCCATTCAGAGGCTAATTGCCACGTCATCCTATTCTCTAAAAAAATTGCCATCAAGAGAAACATTTGTCAATCTCCTGGAG   810
GlyLeuGluSerIleGlnArgLeuIleAlaThrSerSerTyrSerLeuLysLysLeuProSerArgGluThrPheValAsnLeuLeuGlu   270
                                                         866
GCCACGTTGACTTACCCCAGCCACTGCTGTGCTTTTAGAAACTTGCCAACAAAAGAACAGAATTTTTCACATTCCATTTCTGAAAACTTT   900
AlaThrLeuThrTyrProSerHisCysCysAlaPheArgAsnLeuProThrLysGluGlnAsnPheSerHisSerIleSerGluAsnPhe   300
                                                         289
```

FIG. 1B

TCCAAACAATGTGAAAGCACAGTAAGGAAAGTGAGTAACAAAACACTTTATTCTTCCATGCTTGCTGAGAGTGAACTGAGTGGCTGGGAC 990
SerLysGlnCysGluSerThrValArgLysValSerAsnLysThrLeuTyrSerSerMetLeuAlaGluSerGluLeuSerGlyTrpAsp 330

TATGAATATGGTTTCTGCTTACCCAAGACACCCCGATGTGCTCCTGAACCAGATGCTTTTAATCCCTGTGAAGACATTATGGGCTATGAC 1080
TyrGluTyrGlyPheCysLeuProLysThrProArgCysAlaProGluProAspAlaPheAsnProCysGluAspIleMetGlyTyrAsp 360

TTCCTTAGGGTCCTGATTTGGCTGATTAATATTCTAGCCATCATGGGAAACATGACTGTTCTTTTTGTTCTCCTGACAAGTCGTTACAAA 1170
PheLeuArgValLeuIleTrpLeuIleAsnIleLeuAlaIleMetGlyAsnMetThrValLeuPheValLeuLeuThrSerArgTyrLys 390

CTTACAGTGCCTCGTTTTCTCATGTGCAATCTCTCCTTTGCAGACTTTTGCATGGGGCTCTATCTGCTGCTCATAGCCTCAGTTGATTCC 1260
LeuThrValProArgPheLeuMetCysAsnLeuSerPheAlaAspPheCysMetGlyLeuTyrLeuLeuLeuIleAlaSerValAspSer 420

CAAACCAAGGGCCAGTACTATAACCATGCCATAGACTGGCAGACAGGGAGTGGGTGCAGCACTGCTGGCTTTTTCACTGTATTCGCAAGT 1350
GlnThrLysGlyGlnTyrTyrAsnHisAlaIleAspTrpGlnThrGlySerGlyCysSerThrAlaGlyPhePheThrValPheAlaSer 450

GAACTTTCTGTCTACACCCTCACCGTCATCACTCTAGAAAGATGGCACACCATCACCTATGCTATTCACCTGGACCAAAAGCTGCGATTA 1440
GluLeuSerValTyrThrLeuThrValIleThrLeuGluArgTrpHisThrIleThrTyrAlaIleHisLeuAspGlnLysLeuArgLeu 480

AGACATGCCATTCTGATTATGCTTGGAGGATGGCTCTTTTCTTCTCTAATTGCTATGTTGCCCCTTGTCGGTGTCAGCAATTACATGAAG 1530
ArgHisAlaIleLeuIleMetLeuGlyGlyTrpLeuPheSerSerLeuIleAlaMetLeuProLeuValGlyValSerAsnTyrMetLys 510

FIG. 1C

GTCAGTATTTGCTTCCCCATGGATGTGGAAACCACTCTCTCACAAGTCTATATATTAACCATCCTGATTCTCAATGTGGTGGCCTTCTTC 1620
ValSerIleCysPheProMetAspValGluThrThrLeuSerGlnValTyrIleLeuThrIleLeuIleLeuAsnValValAlaPhePhe 540

ATAATTTGTGCTTGCTACATTAAAATTTATTTTGCAGTTCGAAACCCAGAATTAATGGCTACCAATAAAGATACAAAGATTGCTAAGAAA 1710
IleIleCysAlaCysTyrIleLysIleTyrPheAlaValArgAsnProGluLeuMetAlaThrAsnLysAspThrLysIleAlaLysLys 570

ATGGCAATCCTCATCTTCACCGATTTCACCTGCATGGCACCTATCTCTTTTTTTGCCATCTCAGCTGCCTTCAAAGTACCTCTTATCACA 1800
MetAlaIleLeuIlePheThrAspPheThrCysMetAlaProIleSerPhePheAlaIleSerAlaAlaPheLysValProLeuIleThr 600

GTAACCAACTCTAAAGTTTTACTGGTTCTTTTTTATCCCATCAATTCTTGTGCCAATCCATTTCTGTATGCAATATTCACTAAGACATTC 1890
ValThrAsnSerLysValLeuLeuValLeuPheTyrProIleAsnSerCysAlaAsnProPheLeuTyrAlaIlePheThrLysThrPhe 630

CAAAGAGATTTCTTTCTTTTGCTGAGCAAATTTGGCTGCTGTAAACGTCGGGCTGAACTTTATAGAAGGAAAGATTTTTCAGCTTACACC 1980
GlnArgAspPhePheLeuLeuLeuSerLysPheGlyCysCysLysArgArgAlaGluLeuTyrArgArgLysAspPheSerAlaTyrThr 660

TCCAACTGCAAAAATGGCTTCACTGGATCAAATAAGCCTTCTCAATCCACCTTGAAGTTGTCCACATTGCACTGTCAAGGTACAGCTCTC 2070
SerAsnCysLysAsnGlyPheThrGlySerAsnLysProSerGlnSerThrLeuLysLeuSerThrLeuHisCysGlnGlyThrAlaLeu 690

CTAGACAAGACTCGCTACACAGAGTGTTAACTGTTACATCAGTAACTGCATTATTGAATTGTTCTTAAACCTGTAAAAAAAAATTACCTG 2160
LeuAspLysThrArgTyrThrGluCys 699

FIG. 1D

```
TACCAGTAATTTTAACATAAACGGTTGGATTTAGGAAATTATTTATTTTTAGGTACATTAGGCAAGAGACCTCTACCTAGTAGAAAGTGT  2250
AGTCTATGACCACTGCCACACGTAAAAACTATTTGTCATTGTTACATGGCATAAATATGAAGTTGAGAGTGTTTAGAAATTTTTATAGAA  2340
ATTTTGACACAGTAATTTTGTTTGATGAATCTTTTAAAAAACAGAGGAGGTATTTTGCATATCTTTTTTTCATTTTCGTAATTTGTATTG  2430
CATTCTATAAAAATATTAGTTCATAACAGATCAGAAATTTAAAATAAGGGGCTTTTTCCTCAGGTAGTTTGAAAAACACACTCTAGAGAT  2520
GCACTGTTCAATTCGGTACGCACTAGCCACATGTGGCTAAATTAAAATTAAATAAAATGAGAAATGTAGTTTCTCAGTTGCACTACGTTT  2610
CAAGTTCTCAATGCCTACGTCAAGTTCTCAATGCCTACGTGTGACTAGTGCTTACCATACTGGACAGCACAGACACAGAATATTTTCATC  2700
ACCACAGAAAGTTCTATCTGTTCTATTATAGAGACTTTTATGTATGCCCTATCTGGATTCTACTTATTTATAATTTAAGGTAAACATCTG  2790
AAAGCACATTTCAGCCTATTTGCTTAGTGAAACATTAACCTGTAGACTGTAAACTCCTCGTGAGTAGGAACCCTGTCTCAGTGCATTTTG  2880
TTTTCCTGCTTCCTACCTCAAGATCTTGGCAATGGTACACTACAAATGTGCTGAGTTAGAATTACTCTGAAGTTATGAAACATATAATGA  2970
AAACAATTTTTCCGGCC                                                                           2987
```

FIG. 1E

| FIG. 2A |
|---|
| FIG. 2B |
| FIG. 2C |
| FIG. 2D |

FIG. 2

```
hLh/hCGR  MKQRFSAL-QLLKLLLLLQPPLPRALREAL---CPEP-CNCVPDGALR--C------PGPTAGLTR---------LSLAYLPVKVIPSQAFRGLNEVIKIEISQIDSLERIEANAFDN   96
rLh/hCGR  .GR.VP..R...V.AV..LK.SQLQS..LSGSR....-.D.A......--.------...R...A.---------...T.................V......S.............  100
pLh/hCGR  .RR.SL..R--.L.A...L..PLPQT--L.GAP....-.S.R......--.------...R...S.---------...T...I..............V......S....K........   96
hTSHR     .--.PAD.L..VL..D.--------P.DLGGMG.SS.P.E.HQEEDF.VT.KDIQRI.SLPPSTQT---------.K.IETHLRT...H..SN.PNISR.YV.IDVT.QQL.SHS.Y.   99
rFSHR          M..--..VS..AFLGTGSG--CHHWL-------.H.SNRVFL---.------QDSKVTEIPTDLPRNAIE.RFVLTKLR...KGS.A.FGDLE......N.V..V...DV.S.   93

hLh/hCGR  LLNLSEILIQNTKNLRYIEPGAFINLPGLKYLSICNTGIRKFPDVTKVFSSESNFILEICDNLHITTIPGNAFQGMNNESVTLKLYGNGFEEVQSHAFNGTTLTSLELKENVHLEKMH  214
rLh/hCGR  ......L........L.......T...R............TL.....IS...F.................................................I.......IV.....  218
pLh/hCGR  ...............V.......T...R..............L.....I....F...............V.A..........I............I..........I.......A..K...  214
hTSHR     .SKVTH.E.R..R..T..DPD.LKE..L..F.G.F...LKM...L...Y.TDIF.....T..PYM.S..V.....LC..TL.....N...TS..GY.....K.DAVY.NK.KY.TVIY  217
rFSHR     .PK.H..R.EKAN..L..N.E..Q...S.R..L.S....KHL.A.H.IQ.LQ-KVL.D.Q..IN.HIVAR.S.M.LSF...I.W.SK..I..IENC.....Q.DE.N.SD.NN..ELP  211
```

FIG. 2A

```
hLH/hCGR  NGAFRGA-TGPKTLDISSTKLQALPSYGLESIQRLIATSSYSLKKLPSRETFVNLLEATLTYPSHCCAFRN---------------------LPTKE--------QNFSHSISENFS  301
rLH/hCGR  S...Q..-...SI..............H......T...L......T...K.K.TS..V..............---------------------..K..--------....F..F....  305
pLH/hCGR  .D.....-R..SI...................T................K.T...D..............---------------------.....--------....F..FK...  301
hTSHR     KD..G.VYS..SL..V.Q.SVT....K...HLKE...RNTWT.....LSLS.LH.TR.D.SY.......K.QKKIRGILESLMCNESSMQSLRQRKSV--------NALNSPLHQEYE  327
rFSHR     .DV.Q..-S..VI....R..VHS..NH...NLKK.R.R.T.R.....NLDK..T.M..S..........A.---------------------.KRQISELHPICNKSILRQDIDDMT  305

hLH/hCGR  KQCESTV---------RKVSNKTLYSSMLAESE-----------------LSGWD--YEYGFCL-PKTPRCAPEPDAFNPCEDIMGYDFLRVLIWLINILAIMGNMTVLFVLLTSRYK  390
rLH/hCGR  .......---------..AD.E....AIFE.N.-----------------.....--.D....S-...LQ...................A................F..L............  394
pLH/hCGR  ......A---------.RPN.E....AIF....-----------------..D..--.D....S-...LQ..................................V...........H..  390
hTSHR     ENLGDSIVGYKEKSKFQDTH.NAH.YVFFE.Q.DEIIGFGQELKNPQEET.QAF.SH.D.TI.GDSEDHV.T.KS.E..........K...TVV.FVSL..LL..VF..LI....H..  445
rFSHR     QIGDQR.---------SLIDDEPSYG---KG.D-----------------MMYNE--FD.DL.NEVVDVT.S.K...............NI......F.S....T..T...V..T..Q..  392
```

FIG. 2B

```
                    II                                    III                                                   IV
hLH/hCGR  LTVPRFLMCNLSFADFCMGLYLLLIASVDSQTKGQYYNHAIDWQTGSGCSTAGFFTVFASELSVYTLTVITLERWHTITYAIHLDQKLRLRHAILIMLGGWLFSSLIAMLPLVGVSNY  508
rLH/hCGR  .................................................GA.................................VQ.......P.........T..TM......I...  512
pLH/hCGR  .............................A................N...V..................................Q.......P.........T...........S..  508
hTSHR     .N...........A.......M.......LY.HSE...........P..N.............................YA..F.MR..R.M..CA..V...VCCF.L.L.....I.S.  563
rFSHR     .............A...L.I.I.......IH..S..H.Y.......A..DA...................A...........H.MQ.EC.VQ.ASV.VL..T.AFAA.LF.IF.I.S.  510

                              V                                               VI                                 VII
hLH/hCGR  MKVSICFPMDVETTLSQVYILTILILNVVAFFIICACYIKIYFAVRNPELMATNKDTKIAKKMAILIFTDFTCMAPISFFAISAAFKVPLITVTNSKVLLVLFYPINSCANPFLYAIF  626
rLH/hCGR  ......L.....S........S.........VV......R.....Q...T.P.........................................................I......V.............  630
pLH/hCGR  ......L..............................I............Q..............................V......................L..................V.............  626
hTSHR     A.....L...T..P.ALA..VFV.T..I...V.V.C..V...IT....QYNPGD.......R..V......L.......Y.L..IINK.....S...I......L.............  681
rFSHR     ......L...IDSP.....VMAL.V...L..VV..G..TH..LT....TIVSSSS......R..T......L..............SL.......SKA.I......................  628
```

FIG. 2C

```
hLH/hCGR  TKTFQRDFFLLLSKFGCCKRRAELYR------------RKDFSAYTSNCKNGFTGSNKPSQSTLKLSTLHCQGTALLDKTRYTEC
rLH/hCGR  ..A.....L....R...........------------..E............P.AS....A......V...QPIPPRALTH
pLH/hCGR  ..A.R.........S....HQ.....------------.......---..................T..Q..YSTVM...C..KD.
hTSHR     ..F....V.I......I...Q.QA..------------GQRVPPKN.T---DIQVQKVTHEMRQG.HNNEDYYELIEKSHLTPKKQGQISEEYMQTVL
rFSHR     ..N.R....I.......YEMQ.QI..TETSSATHNFHA..SHCSSAPRVT.SYVLVPLNHS.QN
```

FIG. 2D

FUNCTIONAL EXPRESSION OF THE LH/hCG RECEPTOR

SEQUENCE LISTING

```
<160> NUMBER OF SEQ ID NOS: 17

<210> SEQ ID NO 1
<211> LENGTH: 2987
<212> TYPE: DNA
<213> ORGANISM: Homo sapiens
<220> FEATURE:
<221> NAME/KEY: CDS
<222> LOCATION: (1)..(2097)

<400> SEQUENCE: 1

atg aag cag cgg ttc tcg gcg ctg cag ctg ctg aag ctg ctg ctg ctg       48
Met Lys Gln Arg Phe Ser Ala Leu Gln Leu Leu Lys Leu Leu Leu Leu
  1               5                  10                  15

ctg cag ccg ccg ctg cca cga gcg ctg cgc gag gcg ctc tgc cct gag       96
Leu Gln Pro Pro Leu Pro Arg Ala Leu Arg Glu Ala Leu Cys Pro Glu
             20                  25                  30

ccc tgc aac tgc gtg ccc gac ggc gcc ctg cgc tgc ccc ggc ccc acg      144
```

-continued

```
Pro Cys Asn Cys Val Pro Asp Gly Ala Leu Arg Cys Pro Gly Pro Thr
        35                  40                  45

gcc ggt ctc act cga cta tca ctt gcc tac ctc cct gtc aaa gtg atc      192
Ala Gly Leu Thr Arg Leu Ser Leu Ala Tyr Leu Pro Val Lys Val Ile
    50                  55                  60

cca tct caa gct ttc aga gga ctt aat gag gtc ata aaa att gaa atc      240
Pro Ser Gln Ala Phe Arg Gly Leu Asn Glu Val Ile Lys Ile Glu Ile
 65                  70                  75                  80

tct cag att gat tcc ctg gaa agg ata gaa gct aat gcc ttt gac aac      288
Ser Gln Ile Asp Ser Leu Glu Arg Ile Glu Ala Asn Ala Phe Asp Asn
                85                  90                  95

ctc ctc aat ttg tct gaa ata ctg atc cag aac acc aaa aat ctg aga      336
Leu Leu Asn Leu Ser Glu Ile Leu Ile Gln Asn Thr Lys Asn Leu Arg
            100                 105                 110

tac att gag ccc gga gca ttt ata aat ctt ccc gga tta aaa tac ttg      384
Tyr Ile Glu Pro Gly Ala Phe Ile Asn Leu Pro Gly Leu Lys Tyr Leu
        115                 120                 125

agc atc tgt aac aca ggc atc aga aag ttt cca gat gtt acg aag gtc      432
Ser Ile Cys Asn Thr Gly Ile Arg Lys Phe Pro Asp Val Thr Lys Val
    130                 135                 140

ttc tcc tct gaa tca aat ttc att ctg gaa att tgt gat aac tta cac      480
Phe Ser Ser Glu Ser Asn Phe Ile Leu Glu Ile Cys Asp Asn Leu His
145                 150                 155                 160

ata acc acc ata cca gga aat gct ttt caa ggg atg aat aat gaa tct      528
Ile Thr Thr Ile Pro Gly Asn Ala Phe Gln Gly Met Asn Asn Glu Ser
                165                 170                 175

gta aca ctc aaa cta tat gga aat gga ttt gaa gaa gta caa agt cat      576
Val Thr Leu Lys Leu Tyr Gly Asn Gly Phe Glu Glu Val Gln Ser His
            180                 185                 190

gca ttc aat ggg acg aca ctg act tca ctg gag cta aag gaa aac gta      624
Ala Phe Asn Gly Thr Thr Leu Thr Ser Leu Glu Leu Lys Glu Asn Val
        195                 200                 205

cat ctg gag aag atg cac aat gga gcc ttc cgt ggg gcc aca ggg ccg      672
His Leu Glu Lys Met His Asn Gly Ala Phe Arg Gly Ala Thr Gly Pro
    210                 215                 220

aaa acc ttg gat att tct tcc acc aaa ttg cag gcc ctg ccg agc tat      720
Lys Thr Leu Asp Ile Ser Ser Thr Lys Leu Gln Ala Leu Pro Ser Tyr
225                 230                 235                 240

ggc cta gag tcc att cag agg cta att gcc acg tca tcc tat tct cta      768
Gly Leu Glu Ser Ile Gln Arg Leu Ile Ala Thr Ser Ser Tyr Ser Leu
                245                 250                 255

aaa aaa ttg cca tca aga gaa aca ttt gtc aat ctc ctg gag gcc acg      816
Lys Lys Leu Pro Ser Arg Glu Thr Phe Val Asn Leu Leu Glu Ala Thr
            260                 265                 270

ttg act tac ccc agc cac tgc tgt gct ttt aga aac ttg cca aca aaa      864
Leu Thr Tyr Pro Ser His Cys Cys Ala Phe Arg Asn Leu Pro Thr Lys
        275                 280                 285

gaa cag aat ttt tca cat tcc att tct gaa aac ttt tcc aaa caa tgt      912
Glu Gln Asn Phe Ser His Ser Ile Ser Glu Asn Phe Ser Lys Gln Cys
    290                 295                 300

gaa agc aca gta agg aaa gtg agt aac aaa aca ctt tat tct tcc atg      960
Glu Ser Thr Val Arg Lys Val Ser Asn Lys Thr Leu Tyr Ser Ser Met
305                 310                 315                 320

ctt gct gag agt gaa ctg agt ggc tgg gac tat gaa tat ggt ttc tgc     1008
Leu Ala Glu Ser Glu Leu Ser Gly Trp Asp Tyr Glu Tyr Gly Phe Cys
                325                 330                 335

tta ccc aag aca ccc cga tgt gct cct gaa cca gat gct ttt aat ccc     1056
Leu Pro Lys Thr Pro Arg Cys Ala Pro Glu Pro Asp Ala Phe Asn Pro
            340                 345                 350
```

-continued

```
tgt gaa gac att atg ggc tat gac ttc ctt agg gtc ctg att tgg ctg      1104
Cys Glu Asp Ile Met Gly Tyr Asp Phe Leu Arg Val Leu Ile Trp Leu
        355                 360                 365

att aat att cta gcc atc atg gga aac atg act gtt ctt ttt gtt ctc      1152
Ile Asn Ile Leu Ala Ile Met Gly Asn Met Thr Val Leu Phe Val Leu
    370                 375                 380

ctg aca agt cgt tac aaa ctt aca gtg cct cgt ttt ctc atg tgc aat      1200
Leu Thr Ser Arg Tyr Lys Leu Thr Val Pro Arg Phe Leu Met Cys Asn
385                 390                 395                 400

ctc tcc ttt gca gac ttt tgc atg ggg ctc tat ctg ctg ctc ata gcc      1248
Leu Ser Phe Ala Asp Phe Cys Met Gly Leu Tyr Leu Leu Leu Ile Ala
                405                 410                 415

tca gtt gat tcc caa acc aag ggc cag tac tat aac cat gcc ata gac      1296
Ser Val Asp Ser Gln Thr Lys Gly Gln Tyr Tyr Asn His Ala Ile Asp
            420                 425                 430

tgg cag aca ggg agt ggg tgc agc act gct ggc ttt ttc act gta ttc      1344
Trp Gln Thr Gly Ser Gly Cys Ser Thr Ala Gly Phe Phe Thr Val Phe
        435                 440                 445

gca agt gaa ctt tct gtc tac acc ctc acc gtc atc act cta gaa aga      1392
Ala Ser Glu Leu Ser Val Tyr Thr Leu Thr Val Ile Thr Leu Glu Arg
    450                 455                 460

tgg cac acc atc acc tat gct att cac ctg gac caa aag ctg cga tta      1440
Trp His Thr Ile Thr Tyr Ala Ile His Leu Asp Gln Lys Leu Arg Leu
465                 470                 475                 480

aga cat gcc att ctg att atg ctt gga gga tgg ctc ttt tct tct cta      1488
Arg His Ala Ile Leu Ile Met Leu Gly Gly Trp Leu Phe Ser Ser Leu
                485                 490                 495

att gct atg ttg ccc ctt gtc ggt gtc agc aat tac atg aag gtc agt      1536
Ile Ala Met Leu Pro Leu Val Gly Val Ser Asn Tyr Met Lys Val Ser
            500                 505                 510

att tgc ttc ccc atg gat gtg gaa acc act ctc tca caa gtc tat ata      1584
Ile Cys Phe Pro Met Asp Val Glu Thr Thr Leu Ser Gln Val Tyr Ile
        515                 520                 525

tta acc atc ctg att ctc aat gtg gtg gcc ttc ttc ata att tgt gct      1632
Leu Thr Ile Leu Ile Leu Asn Val Val Ala Phe Phe Ile Ile Cys Ala
    530                 535                 540

tgc tac att aaa att tat ttt gca gtt cga aac cca gaa tta atg gct      1680
Cys Tyr Ile Lys Ile Tyr Phe Ala Val Arg Asn Pro Glu Leu Met Ala
545                 550                 555                 560

acc aat aaa gat aca aag att gct aag aaa atg gca atc ctc atc ttc      1728
Thr Asn Lys Asp Thr Lys Ile Ala Lys Lys Met Ala Ile Leu Ile Phe
                565                 570                 575

acc gat ttc acc tgc atg gca cct atc tct ttt ttt gcc atc tca gct      1776
Thr Asp Phe Thr Cys Met Ala Pro Ile Ser Phe Phe Ala Ile Ser Ala
            580                 585                 590

gcc ttc aaa gta cct ctt atc aca gta acc aac tct aaa gtt tta ctg      1824
Ala Phe Lys Val Pro Leu Ile Thr Val Thr Asn Ser Lys Val Leu Leu
        595                 600                 605

gtt ctt ttt tat ccc atc aat tct tgt gcc aat cca ttt ctg tat gca      1872
Val Leu Phe Tyr Pro Ile Asn Ser Cys Ala Asn Pro Phe Leu Tyr Ala
    610                 615                 620

ata ttc act aag aca ttc caa aga gat ttc ttt ctt ttg ctg agc aaa      1920
Ile Phe Thr Lys Thr Phe Gln Arg Asp Phe Phe Leu Leu Leu Ser Lys
625                 630                 635                 640

ttt ggc tgc tgt aaa cgt cgg gct gaa ctt tat aga agg aaa gat ttt      1968
Phe Gly Cys Cys Lys Arg Arg Ala Glu Leu Tyr Arg Arg Lys Asp Phe
                645                 650                 655

tca gct tac acc tcc aac tgc aaa aat ggc ttc act gga tca aat aag      2016
Ser Ala Tyr Thr Ser Asn Cys Lys Asn Gly Phe Thr Gly Ser Asn Lys
            660                 665                 670
```

-continued

```
cct tct caa tcc acc ttg aag ttg tcc aca ttg cac tgt caa ggt aca     2064
Pro Ser Gln Ser Thr Leu Lys Leu Ser Thr Leu His Cys Gln Gly Thr
        675                 680                 685

gct ctc cta gac aag act cgc tac aca gag tgt taactgttac atcagtaact   2117
Ala Leu Leu Asp Lys Thr Arg Tyr Thr Glu Cys
    690                 695

gcattattga attgttctta aacctgtaaa aaaaaattac ctgtaccagt aattttaaca   2177

taaagggttg gatttaggaa attatttatt tttaggtaca ttaggcaaga gacctctacc   2237

tagtagaaag tgtagtctat gaccactgcc acacgtaaaa actatttgtc attgttacat   2297

ggcataaata tgaagttgag agtgtttaga aatttttata gaaattttga cacagtaatt   2357

ttgtttgatg aatcttttaa aaaacagagg aggtattttg catatctttt tttcattttc   2417

gtaatttgta ttgcattcta taaaaatatt agttcataac agatcagaaa tttaaaataa   2477

ggggcttttt cctcaggtag tttgaaaaac acactctaga gatgcactgt tcaattcggt   2537

acgcactagc cacatgtggc taaattaaaa ttaaataaaa tgagaaatgt agtttctcag   2597

ttgcactacg tttcaagttc tcaatggcta cgtcaagttc tcaatggcta cgtgtgacta   2657

gtgcttacca tactggacag cacagacaca gaatattttc atcaccacag aaagttctat   2717

ctgttctatt atagagactt ttatgtatgc cctatctgga ttctacttat ttataattta   2777

aggtaaacat ctgaaagcac atttcagcct atttgcttag tgaaacatta agctgtagac   2837

tgtaaactcc tcgtgagtag gaaccctgtc tcagtgcatt ttgttttcct gcttcctacc   2897

tcaagatctt ggcaatggta cactacaaat gtgctgagtt agaattactc tgaagttatg   2957

aaacatataa tgaaaacaat ttttccggcc                                     2987


<210> SEQ ID NO 2
<211> LENGTH: 699
<212> TYPE: PRT
<213> ORGANISM: Homo sapiens

<400> SEQUENCE: 2

Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Gly Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
                165                 170                 175
```

-continued

```
Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Leu Asp Ile Ser Ser Thr Lys Leu Gln Ala Leu Pro Ser Tyr
225                 230                 235                 240

Gly Leu Glu Ser Ile Gln Arg Leu Ile Ala Thr Ser Ser Tyr Ser Leu
                245                 250                 255

Lys Lys Leu Pro Ser Arg Glu Thr Phe Val Asn Leu Leu Glu Ala Thr
            260                 265                 270

Leu Thr Tyr Pro Ser His Cys Cys Ala Phe Arg Asn Leu Pro Thr Lys
        275                 280                 285

Glu Gln Asn Phe Ser His Ser Ile Ser Glu Asn Phe Ser Lys Gln Cys
    290                 295                 300

Glu Ser Thr Val Arg Lys Val Ser Asn Lys Thr Leu Tyr Ser Ser Met
305                 310                 315                 320

Leu Ala Glu Ser Glu Leu Ser Gly Trp Asp Tyr Glu Tyr Gly Phe Cys
                325                 330                 335

Leu Pro Lys Thr Pro Arg Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365

Ile Asn Ile Leu Ala Ile Met Gly Asn Met Thr Val Leu Phe Val Leu
    370                 375                 380

Leu Thr Ser Arg Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ser Gln Thr Lys Gly Gln Tyr Tyr Asn His Ala Ile Asp
            420                 425                 430

Trp Gln Thr Gly Ser Gly Cys Ser Thr Ala Gly Phe Phe Thr Val Phe
        435                 440                 445

Ala Ser Glu Leu Ser Val Tyr Thr Leu Thr Val Ile Thr Leu Glu Arg
    450                 455                 460

Trp His Thr Ile Thr Tyr Ala Ile His Leu Asp Gln Lys Leu Arg Leu
465                 470                 475                 480

Arg His Ala Ile Leu Ile Met Leu Gly Gly Trp Leu Phe Ser Ser Leu
                485                 490                 495

Ile Ala Met Leu Pro Leu Val Gly Val Ser Asn Tyr Met Lys Val Ser
            500                 505                 510

Ile Cys Phe Pro Met Asp Val Glu Thr Thr Leu Ser Gln Val Tyr Ile
        515                 520                 525

Leu Thr Ile Leu Ile Leu Asn Val Val Ala Phe Phe Ile Ile Cys Ala
    530                 535                 540

Cys Tyr Ile Lys Ile Tyr Phe Ala Val Arg Asn Pro Glu Leu Met Ala
545                 550                 555                 560

Thr Asn Lys Asp Thr Lys Ile Ala Lys Lys Met Ala Ile Leu Ile Phe
                565                 570                 575

Thr Asp Phe Thr Cys Met Ala Pro Ile Ser Phe Phe Ala Ile Ser Ala
            580                 585                 590
```

-continued

```
Ala Phe Lys Val Pro Leu Ile Thr Val Thr Asn Ser Lys Val Leu Leu
        595                 600                 605

Val Leu Phe Tyr Pro Ile Asn Ser Cys Ala Asn Pro Phe Leu Tyr Ala
    610                 615                 620

Ile Phe Thr Lys Thr Phe Gln Arg Asp Phe Phe Leu Leu Leu Ser Lys
625                 630                 635                 640

Phe Gly Cys Cys Lys Arg Arg Ala Glu Leu Tyr Arg Arg Lys Asp Phe
                645                 650                 655

Ser Ala Tyr Thr Ser Asn Cys Lys Asn Gly Phe Thr Gly Ser Asn Lys
            660                 665                 670

Pro Ser Gln Ser Thr Leu Lys Leu Ser Thr Leu His Cys Gln Gly Thr
        675                 680                 685

Ala Leu Leu Asp Lys Thr Arg Tyr Thr Glu Cys
    690                 695


<210> SEQ ID NO 3
<211> LENGTH: 700
<212> TYPE: PRT
<213> ORGANISM: Rattus sp.

<400> SEQUENCE: 3

Met Gly Arg Arg Val Pro Ala Leu Arg Gln Leu Leu Val Leu Ala Val
  1               5                  10                  15

Leu Leu Leu Lys Pro Ser Gln Leu Gln Ser Arg Glu Leu Ser Gly Ser
             20                  25                  30

Arg Cys Pro Glu Pro Cys Asp Cys Ala Pro Asp Gly Ala Leu Arg Cys
         35                  40                  45

Pro Gly Pro Arg Ala Gly Leu Ala Arg Leu Ser Leu Thr Tyr Leu Pro
     50                  55                  60

Val Lys Val Ile Pro Ser Gln Ala Phe Arg Gly Leu Asn Glu Val Val
 65                  70                  75                  80

Lys Ile Glu Ile Ser Gln Ser Asp Ser Leu Glu Arg Ile Glu Ala Asn
                 85                  90                  95

Ala Phe Asp Asn Leu Leu Asn Leu Ser Glu Leu Leu Ile Gln Asn Thr
            100                 105                 110

Lys Asn Leu Leu Tyr Ile Glu Pro Gly Ala Phe Thr Asn Leu Pro Arg
        115                 120                 125

Leu Lys Tyr Leu Ser Ile Cys Asn Thr Gly Ile Arg Thr Leu Pro Asp
    130                 135                 140

Val Thr Lys Ile Ser Ser Ser Glu Phe Asn Phe Ile Leu Glu Ile Cys
145                 150                 155                 160

Asp Asn Leu His Ile Thr Thr Ile Pro Gly Asn Ala Phe Gln Gly Met
                165                 170                 175

Asn Asn Glu Ser Val Thr Leu Lys Leu Tyr Gly Asn Gly Phe Glu Glu
            180                 185                 190

Val Gln Ser His Ala Phe Asn Gly Thr Thr Leu Ile Ser Leu Glu Leu
        195                 200                 205

Lys Glu Asn Ile Tyr Leu Glu Lys Met His Ser Gly Ala Phe Gln Gly
    210                 215                 220

Ala Thr Gly Pro Ser Ile Leu Asp Ile Ser Ser Thr Lys Leu Gln Ala
225                 230                 235                 240

Leu Pro Ser His Gly Leu Glu Ser Ile Gln Thr Leu Ile Ala Leu Ser
                245                 250                 255

Ser Tyr Ser Leu Lys Thr Leu Pro Ser Lys Glu Lys Phe Thr Ser Leu
            260                 265                 270
```

-continued

```
Leu Val Ala Thr Leu Thr Tyr Pro Ser His Cys Cys Ala Phe Arg Asn
        275                 280                 285

Leu Pro Lys Lys Glu Gln Asn Phe Ser Phe Ser Ile Phe Glu Asn Phe
    290                 295                 300

Ser Lys Gln Cys Glu Ser Thr Val Arg Lys Ala Asp Asn Glu Thr Leu
305                 310                 315                 320

Tyr Ser Ala Ile Phe Glu Glu Asn Glu Leu Ser Gly Trp Asp Tyr Asp
                325                 330                 335

Tyr Gly Phe Cys Ser Pro Lys Thr Leu Gln Cys Ala Pro Glu Pro Asp
            340                 345                 350

Ala Phe Asn Pro Cys Glu Asp Ile Met Gly Tyr Ala Phe Leu Arg Val
        355                 360                 365

Leu Ile Trp Leu Ile Asn Ile Leu Ala Ile Phe Gly Asn Leu Thr Val
    370                 375                 380

Leu Phe Val Leu Leu Thr Ser Arg Tyr Lys Leu Thr Val Pro Arg Phe
385                 390                 395                 400

Leu Met Cys Asn Leu Ser Phe Ala Asp Phe Cys Met Gly Leu Tyr Leu
                405                 410                 415

Leu Leu Ile Ala Ser Val Asp Ser Gln Thr Lys Gly Gln Tyr Tyr Asn
            420                 425                 430

His Ala Ile Asp Trp Gln Thr Gly Ser Gly Cys Gly Ala Ala Gly Phe
        435                 440                 445

Phe Thr Val Phe Ala Ser Glu Leu Ser Val Tyr Thr Leu Thr Val Ile
    450                 455                 460

Thr Leu Glu Arg Trp His Thr Ile Thr Tyr Ala Val Gln Leu Asp Gln
465                 470                 475                 480

Lys Leu Arg Leu Arg His Ala Ile Pro Ile Met Leu Gly Gly Trp Leu
                485                 490                 495

Phe Ser Thr Leu Ile Ala Thr Met Pro Leu Val Gly Ile Ser Asn Tyr
            500                 505                 510

Met Lys Val Ser Ile Cys Leu Pro Met Asp Val Glu Ser Thr Leu Ser
        515                 520                 525

Gln Val Tyr Ile Leu Ser Ile Leu Ile Leu Asn Val Val Ala Phe Val
    530                 535                 540

Val Ile Cys Ala Cys Tyr Ile Arg Ile Tyr Phe Ala Val Gln Asn Pro
545                 550                 555                 560

Glu Leu Thr Ala Pro Asn Lys Asp Thr Lys Ile Ala Lys Lys Met Ala
                565                 570                 575

Ile Leu Ile Phe Thr Asp Phe Thr Cys Met Ala Pro Ile Ser Phe Phe
            580                 585                 590

Ala Ile Ser Ala Ala Phe Lys Val Pro Leu Ile Thr Val Thr Asn Ser
        595                 600                 605

Lys Ile Leu Leu Val Leu Phe Tyr Pro Val Asn Ser Cys Ala Asn Pro
    610                 615                 620

Phe Leu Tyr Ala Ile Phe Thr Lys Ala Phe Gln Arg Asp Phe Leu Leu
625                 630                 635                 640

Leu Leu Ser Arg Phe Gly Cys Cys Lys Arg Arg Ala Glu Leu Tyr Arg
                645                 650                 655

Arg Lys Glu Phe Ser Ala Tyr Thr Ser Asn Cys Lys Asn Gly Phe Pro
            660                 665                 670

Gly Ala Ser Lys Pro Ser Gln Ala Thr Leu Lys Leu Ser Thr Val His
        675                 680                 685
```

-continued

```
Cys Gln Gln Pro Ile Pro Pro Arg Ala Leu Thr His
    690                 695                 700


<210> SEQ ID NO 4
<211> LENGTH: 696
<212> TYPE: PRT
<213> ORGANISM: Sus scrofa

<400> SEQUENCE: 4

Met Arg Arg Arg Ser Leu Ala Leu Arg Leu Leu Leu Ala Leu Leu Leu
  1               5                  10                  15

Leu Pro Pro Pro Leu Pro Gln Thr Leu Leu Gly Ala Pro Cys Pro Glu
             20                  25                  30

Pro Cys Ser Cys Arg Pro Asp Gly Ala Leu Arg Cys Pro Gly Pro Arg
         35                  40                  45

Ala Gly Leu Ser Arg Leu Ser Leu Thr Tyr Leu Thr Ile Lys Val Ile
     50                  55                  60

Pro Ser Gln Ala Phe Arg Gly Leu Asn Glu Val Val Lys Ile Glu Ile
 65                  70                  75                  80

Ser Gln Ser Asp Ser Leu Glu Lys Ile Glu Ala Asn Ala Phe Asp Asn
                 85                  90                  95

Leu Leu Asn Leu Ser Glu Ile Leu Ile Gln Asn Thr Lys Asn Leu Val
            100                 105                 110

Tyr Ile Glu Pro Gly Ala Phe Thr Asn Leu Pro Arg Leu Lys Tyr Leu
        115                 120                 125

Ser Ile Cys Asn Thr Gly Ile Arg Lys Leu Pro Asp Val Thr Lys Ile
    130                 135                 140

Phe Ser Ser Glu Phe Asn Phe Ile Leu Glu Ile Cys Asp Asn Leu His
145                 150                 155                 160

Ile Thr Thr Val Pro Ala Asn Ala Phe Gln Gly Met Asn Asn Glu Ser
                165                 170                 175

Ile Thr Leu Lys Leu Tyr Gly Asn Gly Phe Glu Glu Ile Gln Ser His
            180                 185                 190

Ala Phe Asn Gly Thr Thr Leu Ile Ser Leu Glu Leu Lys Glu Asn Ala
        195                 200                 205

His Leu Lys Lys Met His Asn Asp Ala Phe Arg Gly Ala Arg Gly Pro
    210                 215                 220

Ser Ile Leu Asp Ile Ser Ser Thr Lys Leu Gln Ala Leu Pro Ser Tyr
225                 230                 235                 240

Gly Leu Glu Ser Ile Gln Thr Leu Ile Ala Thr Ser Ser Tyr Ser Leu
                245                 250                 255

Lys Lys Leu Pro Ser Arg Glu Lys Phe Thr Asn Leu Leu Asp Ala Thr
            260                 265                 270

Leu Thr Tyr Pro Ser His Cys Cys Ala Phe Arg Asn Leu Pro Thr Lys
        275                 280                 285

Glu Gln Asn Phe Ser Phe Ser Ile Phe Lys Asn Phe Ser Lys Gln Cys
    290                 295                 300

Glu Ser Thr Ala Arg Arg Pro Asn Asn Glu Thr Leu Tyr Ser Ala Ile
305                 310                 315                 320

Phe Ala Glu Ser Glu Leu Ser Asp Trp Asp Tyr Asp Tyr Gly Phe Cys
                325                 330                 335

Ser Pro Lys Thr Leu Gln Cys Ala Pro Glu Pro Asp Ala Phe Asn Pro
            340                 345                 350

Cys Glu Asp Ile Met Gly Tyr Asp Phe Leu Arg Val Leu Ile Trp Leu
        355                 360                 365
```

-continued

```
Ile Asn Ile Leu Ala Ile Met Gly Asn Val Thr Val Leu Phe Val Leu
    370                 375                 380

Leu Thr Ser His Tyr Lys Leu Thr Val Pro Arg Phe Leu Met Cys Asn
385                 390                 395                 400

Leu Ser Phe Ala Asp Phe Cys Met Gly Leu Tyr Leu Leu Leu Ile Ala
                405                 410                 415

Ser Val Asp Ala Gln Thr Lys Gly Gln Tyr Tyr Asn His Ala Ile Asp
            420                 425                 430

Trp Gln Thr Gly Asn Gly Cys Ser Val Ala Gly Phe Phe Thr Val Phe
        435                 440                 445

Ala Ser Glu Leu Ser Val Tyr Thr Leu Thr Val Ile Thr Leu Glu Arg
    450                 455                 460

Trp His Thr Ile Thr Tyr Ala Ile Gln Leu Asp Gln Lys Leu Arg Leu
465                 470                 475                 480

Arg His Ala Ile Pro Ile Met Leu Gly Gly Trp Leu Phe Ser Thr Leu
                485                 490                 495

Ile Ala Met Leu Pro Leu Val Gly Val Ser Ser Tyr Met Lys Val Ser
            500                 505                 510

Ile Cys Leu Pro Met Asp Val Glu Thr Thr Leu Ser Gln Val Tyr Ile
        515                 520                 525

Leu Thr Ile Leu Ile Leu Asn Val Val Ala Phe Ile Ile Ile Cys Ala
    530                 535                 540

Cys Tyr Ile Lys Ile Tyr Phe Ala Val Gln Asn Pro Glu Leu Met Ala
545                 550                 555                 560

Thr Asn Lys Asp Thr Lys Ile Ala Lys Lys Met Ala Val Leu Ile Phe
                565                 570                 575

Thr Asp Phe Thr Cys Met Ala Pro Ile Ser Phe Phe Ala Ile Ser Ala
            580                 585                 590

Ala Leu Lys Val Pro Leu Ile Thr Val Thr Asn Ser Lys Val Leu Leu
        595                 600                 605

Val Leu Phe Tyr Pro Val Asn Ser Cys Ala Asn Pro Phe Leu Tyr Ala
    610                 615                 620

Ile Phe Thr Lys Ala Phe Arg Arg Asp Phe Phe Leu Leu Leu Ser Lys
625                 630                 635                 640

Ser Gly Cys Cys Lys His Gln Ala Glu Leu Tyr Arg Arg Lys Asp Phe
                645                 650                 655

Ser Ala Tyr Cys Lys Asn Gly Phe Thr Gly Ser Asn Lys Pro Ser Gln
            660                 665                 670

Ser Thr Leu Lys Leu Thr Thr Leu Gln Cys Gln Tyr Ser Thr Val Met
        675                 680                 685

Asp Lys Thr Cys Tyr Lys Asp Cys
    690                 695


<210> SEQ ID NO 5
<211> LENGTH: 764
<212> TYPE: PRT
<213> ORGANISM: Homo sapiens

<400> SEQUENCE: 5

Met Arg Pro Ala Asp Leu Leu Gln Leu Val Leu Leu Leu Asp Leu Pro
  1               5                  10                  15

Arg Asp Leu Gly Gly Met Gly Cys Ser Ser Pro Pro Cys Glu Cys His
             20                  25                  30

Gln Glu Glu Asp Phe Arg Val Thr Cys Lys Asp Ile Gln Arg Ile Pro
```

-continued

```
        35                  40                  45

Ser Leu Pro Pro Ser Thr Gln Thr Leu Lys Leu Ile Glu Thr His Leu
    50                  55                  60

Arg Thr Ile Pro Ser His Ala Phe Ser Asn Leu Pro Asn Ile Ser Arg
65                  70                  75                  80

Ile Tyr Val Ser Ile Asp Val Thr Leu Gln Gln Leu Glu Ser His Ser
                85                  90                  95

Phe Tyr Asn Leu Ser Lys Val Thr His Ile Glu Ile Arg Asn Thr Arg
            100                 105                 110

Asn Leu Thr Tyr Ile Asp Pro Asp Ala Leu Lys Glu Leu Pro Leu Leu
        115                 120                 125

Lys Phe Leu Gly Ile Phe Asn Thr Gly Leu Lys Met Phe Pro Asp Leu
    130                 135                 140

Thr Lys Val Tyr Ser Thr Asp Ile Phe Phe Ile Leu Glu Ile Thr Asp
145                 150                 155                 160

Asn Pro Tyr Met Thr Ser Ile Pro Val Asn Ala Phe Gln Gly Leu Cys
                165                 170                 175

Asn Glu Thr Leu Thr Leu Lys Leu Tyr Asn Asn Gly Phe Thr Ser Val
            180                 185                 190

Gln Gly Tyr Ala Phe Asn Gly Thr Lys Leu Asp Ala Val Tyr Leu Asn
        195                 200                 205

Lys Asn Lys Tyr Leu Thr Val Ile Tyr Lys Asp Ala Phe Gly Gly Val
    210                 215                 220

Tyr Ser Gly Pro Ser Leu Leu Asp Val Ser Gln Thr Ser Val Thr Ala
225                 230                 235                 240

Leu Pro Ser Lys Gly Leu Glu His Leu Lys Glu Leu Ile Ala Arg Asn
                245                 250                 255

Thr Trp Thr Leu Lys Lys Leu Pro Leu Ser Leu Ser Phe Leu His Leu
            260                 265                 270

Thr Arg Ala Asp Leu Ser Tyr Pro Ser His Cys Cys Ala Phe Lys Asn
        275                 280                 285

Gln Lys Lys Ile Arg Gly Ile Leu Glu Ser Leu Met Cys Asn Glu Ser
    290                 295                 300

Ser Met Gln Ser Leu Arg Gln Arg Lys Ser Val Asn Ala Leu Asn Ser
305                 310                 315                 320

Pro Leu His Gln Glu Tyr Glu Glu Asn Leu Gly Asp Ser Ile Val Gly
                325                 330                 335

Tyr Lys Glu Lys Ser Lys Phe Gln Asp Thr His Asn Asn Ala His Tyr
            340                 345                 350

Tyr Val Phe Phe Glu Glu Gln Glu Asp Glu Ile Ile Gly Phe Gly Gln
        355                 360                 365

Glu Leu Lys Asn Pro Gln Glu Glu Thr Leu Gln Ala Phe Asp Ser His
    370                 375                 380

Tyr Asp Tyr Thr Ile Cys Gly Asp Ser Glu Asp Met Val Cys Thr Pro
385                 390                 395                 400

Lys Ser Asp Glu Phe Asn Pro Cys Glu Asp Ile Met Gly Tyr Lys Phe
                405                 410                 415

Leu Arg Ile Val Val Trp Phe Val Ser Leu Leu Ala Leu Leu Gly Asn
            420                 425                 430

Val Phe Val Leu Leu Ile Leu Leu Thr Ser His Tyr Lys Leu Asn Val
        435                 440                 445

Pro Arg Phe Leu Met Cys Asn Leu Ala Phe Ala Asp Phe Cys Met Gly
    450                 455                 460
```

```
Met Tyr Leu Leu Leu Ile Ala Ser Val Asp Leu Tyr Thr His Ser Glu
465                 470                 475                 480

Tyr Tyr Asn His Ala Ile Asp Trp Gln Thr Gly Pro Gly Cys Asn Thr
                485                 490                 495

Ala Gly Phe Phe Thr Val Phe Ala Ser Glu Leu Ser Val Tyr Thr Leu
            500                 505                 510

Thr Val Ile Thr Leu Glu Arg Trp Tyr Ala Ile Thr Phe Ala Met Arg
        515                 520                 525

Leu Asp Arg Lys Met Arg Leu Arg His Ala Cys Ala Ile Met Val Gly
    530                 535                 540

Gly Trp Val Cys Cys Phe Leu Leu Ala Leu Leu Pro Leu Val Gly Ile
545                 550                 555                 560

Ser Ser Tyr Ala Lys Val Ser Ile Cys Leu Pro Met Asp Thr Glu Thr
                565                 570                 575

Pro Leu Ala Leu Ala Tyr Ile Val Phe Val Leu Thr Leu Asn Ile Val
            580                 585                 590

Ala Phe Val Ile Val Cys Cys Cys Tyr Val Lys Ile Tyr Ile Thr Val
        595                 600                 605

Arg Asn Pro Gln Tyr Asn Pro Gly Asp Lys Asp Thr Lys Ile Ala Lys
    610                 615                 620

Arg Met Ala Val Leu Ile Phe Thr Asp Phe Ile Cys Met Ala Pro Ile
625                 630                 635                 640

Ser Phe Tyr Ala Leu Ser Ala Ile Leu Asn Lys Pro Leu Ile Thr Val
                645                 650                 655

Ser Asn Ser Lys Ile Leu Leu Val Leu Phe Tyr Pro Leu Asn Ser Cys
            660                 665                 670

Ala Asn Pro Phe Leu Tyr Ala Ile Phe Thr Lys Glu Phe Gln Arg Asp
        675                 680                 685

Val Phe Ile Leu Leu Ser Lys Phe Gly Ile Cys Lys Arg Gln Ala Gln
    690                 695                 700

Ala Tyr Arg Gly Gln Arg Val Pro Pro Lys Asn Ser Thr Asp Ile Gln
705                 710                 715                 720

Val Gln Lys Val Thr His Glu Met Arg Gln Gly Leu His Asn Met Glu
                725                 730                 735

Asp Val Tyr Glu Leu Ile Glu Lys Ser His Leu Thr Pro Lys Lys Gln
            740                 745                 750

Gly Gln Ile Ser Glu Glu Tyr Met Gln Thr Val Leu
        755                 760


<210> SEQ ID NO 6
<211> LENGTH: 692
<212> TYPE: PRT
<213> ORGANISM: Rattus sp.

<400> SEQUENCE: 6

Met Ala Leu Leu Leu Val Ser Leu Leu Ala Phe Leu Gly Thr Gly Ser
  1               5                  10                  15

Gly Cys His His Trp Leu Cys His Cys Ser Asn Arg Val Phe Leu Cys
             20                  25                  30

Gln Asp Ser Lys Val Thr Glu Ile Pro Thr Asp Leu Pro Arg Asn Ala
         35                  40                  45

Ile Glu Leu Arg Phe Val Leu Thr Lys Leu Arg Val Ile Pro Lys Gly
     50                  55                  60

Ser Phe Ala Gly Phe Gly Asp Leu Glu Lys Ile Glu Ile Ser Gln Asn
```

-continued

```
65                  70                  75                  80

Asp Val Leu Glu Val Ile Glu Ala Asp Val Phe Ser Asn Leu Pro Lys
                85                  90                  95

Leu His Glu Ile Arg Ile Glu Lys Ala Asn Asn Leu Leu Tyr Ile Asn
            100                 105                 110

Pro Glu Ala Phe Gln Asn Leu Pro Ser Leu Arg Tyr Leu Leu Ile Ser
        115                 120                 125

Asn Thr Gly Ile Lys His Leu Pro Ala Val His Lys Ile Gln Ser Leu
    130                 135                 140

Gln Lys Val Leu Leu Asp Ile Gln Asp Asn Ile Asn Ile His Ile Val
145                 150                 155                 160

Ala Arg Asn Ser Phe Met Gly Leu Ser Phe Glu Ser Val Ile Leu Trp
                165                 170                 175

Leu Ser Lys Asn Gly Ile Glu Glu Ile His Asn Cys Ala Phe Asn Gly
            180                 185                 190

Thr Gln Leu Asp Glu Leu Asn Leu Ser Asp Asn Asn Asn Leu Glu Glu
        195                 200                 205

Leu Pro Asn Asp Val Phe Gln Gly Ala Ser Gly Pro Val Ile Leu Asp
    210                 215                 220

Ile Ser Arg Thr Lys Val His Ser Leu Pro Asn His Gly Leu Glu Asn
225                 230                 235                 240

Leu Lys Lys Leu Arg Ala Arg Ser Thr Tyr Arg Leu Lys Lys Leu Pro
                245                 250                 255

Asn Leu Asp Lys Phe Val Thr Leu Met Glu Ala Ser Leu Thr Tyr Pro
            260                 265                 270

Ser His Cys Cys Ala Phe Ala Asn Leu Lys Arg Gln Ile Ser Glu Leu
        275                 280                 285

His Pro Ile Cys Asn Lys Ser Ile Leu Arg Gln Asp Ile Asp Asp Met
    290                 295                 300

Thr Gln Ile Gly Asp Gln Arg Val Ser Leu Ile Asp Asp Glu Pro Ser
305                 310                 315                 320

Tyr Gly Lys Gly Ser Asp Met Met Tyr Asn Glu Phe Asp Tyr Asp Leu
                325                 330                 335

Cys Asn Glu Val Val Asp Val Thr Cys Ser Pro Lys Pro Asp Ala Phe
            340                 345                 350

Asn Pro Cys Glu Asp Ile Met Gly Tyr Asn Ile Leu Arg Val Leu Ile
        355                 360                 365

Trp Phe Ile Ser Ile Leu Ala Ile Thr Gly Asn Thr Thr Val Leu Val
    370                 375                 380

Val Leu Thr Thr Ser Gln Tyr Lys Leu Thr Val Pro Arg Phe Leu Met
385                 390                 395                 400

Cys Asn Leu Ala Phe Ala Asp Leu Cys Ile Gly Ile Tyr Leu Leu Leu
                405                 410                 415

Ile Ala Ser Val Asp Ile His Thr Lys Ser Gln Tyr His Asn Tyr Ala
            420                 425                 430

Ile Asp Trp Gln Thr Gly Ala Gly Cys Asp Ala Ala Gly Phe Phe Thr
        435                 440                 445

Val Phe Ala Ser Glu Leu Ser Val Tyr Thr Leu Thr Ala Ile Thr Leu
    450                 455                 460

Glu Arg Trp His Thr Ile Thr His Ala Met Gln Leu Glu Cys Lys Val
465                 470                 475                 480

Gln Leu Arg His Ala Ala Ser Val Met Val Leu Gly Trp Thr Phe Ala
                485                 490                 495
```

-continued

```
Phe Ala Ala Ala Leu Phe Pro Ile Phe Gly Ile Ser Ser Tyr Met Lys
            500                 505                 510

Val Ser Ile Cys Leu Pro Met Asp Ile Asp Ser Pro Leu Ser Gln Leu
        515                 520                 525

Tyr Val Met Ala Leu Leu Val Leu Asn Val Leu Ala Phe Val Val Ile
    530                 535                 540

Cys Gly Cys Tyr Thr His Ile Tyr Leu Thr Val Arg Asn Pro Thr Ile
545                 550                 555                 560

Val Ser Ser Ser Ser Asp Thr Lys Ile Ala Lys Arg Met Ala Thr Leu
                565                 570                 575

Ile Phe Thr Asp Phe Leu Cys Met Ala Pro Ile Ser Phe Phe Ala Ile
            580                 585                 590

Ser Ala Ser Leu Lys Val Pro Leu Ile Thr Val Ser Lys Ala Lys Ile
        595                 600                 605

Leu Leu Val Leu Phe Tyr Pro Ile Asn Ser Cys Ala Asn Pro Phe Leu
    610                 615                 620

Tyr Ala Ile Phe Thr Lys Asn Phe Arg Arg Asp Phe Phe Ile Leu Leu
625                 630                 635                 640

Ser Lys Phe Gly Cys Tyr Glu Met Gln Ala Gln Ile Tyr Arg Thr Glu
                645                 650                 655

Thr Ser Ser Ala Thr His Asn Phe His Ala Arg Lys Ser His Cys Ser
            660                 665                 670

Ser Ala Pro Arg Val Thr Asn Ser Tyr Val Leu Val Pro Leu Asn His
        675                 680                 685

Ser Ser Gln Asn
    690


<210> SEQ ID NO 7
<211> LENGTH: 636
<212> TYPE: PRT
<213> ORGANISM: Homo sapiens

<400> SEQUENCE: 7

Met Lys Gln Arg Phe Ser Ala Leu Gln Leu Leu Lys Leu Leu Leu Leu
  1               5                  10                  15

Leu Gln Pro Pro Leu Pro Arg Ala Leu Arg Glu Ala Leu Cys Pro Glu
             20                  25                  30

Pro Cys Asn Cys Val Pro Asp Gly Ala Leu Arg Cys Pro Gly Pro Thr
         35                  40                  45

Ala Gly Leu Thr Arg Leu Ser Leu Ala Tyr Leu Pro Val Lys Val Ile
     50                  55                  60

Pro Ser Gln Ala Phe Arg Gly Leu Asn Glu Val Ile Lys Ile Glu Ile
 65                  70                  75                  80

Ser Gln Ile Asp Ser Leu Glu Arg Ile Glu Ala Asn Ala Phe Asp Asn
                 85                  90                  95

Leu Leu Asn Leu Ser Glu Ile Leu Ile Gln Asn Thr Lys Asn Leu Arg
            100                 105                 110

Tyr Ile Glu Pro Gly Ala Phe Ile Asn Leu Pro Gly Leu Lys Tyr Leu
        115                 120                 125

Ser Ile Cys Asn Thr Gly Ile Arg Lys Phe Pro Asp Val Thr Lys Val
    130                 135                 140

Phe Ser Ser Glu Ser Asn Phe Ile Leu Glu Ile Cys Asp Asn Leu His
145                 150                 155                 160

Ile Thr Thr Ile Pro Gly Asn Ala Phe Gln Gly Met Asn Asn Glu Ser
```

-continued

```
                165                 170                 175

Val Thr Leu Lys Leu Tyr Gly Asn Gly Phe Glu Glu Val Gln Ser His
            180                 185                 190

Ala Phe Asn Gly Thr Thr Leu Thr Ser Leu Glu Leu Lys Glu Asn Val
        195                 200                 205

His Leu Glu Lys Met His Asn Gly Ala Phe Arg Gly Ala Thr Gly Pro
    210                 215                 220

Lys Thr Gln Asn Phe Ser His Ser Ile Ser Glu Asn Phe Ser Lys Gln
225                 230                 235                 240

Cys Glu Ser Thr Val Arg Lys Val Ser Asn Lys Thr Leu Tyr Ser Ser
                245                 250                 255

Met Leu Ala Glu Ser Glu Leu Ser Gly Trp Asp Tyr Glu Tyr Gly Phe
            260                 265                 270

Cys Leu Pro Lys Thr Pro Arg Cys Ala Pro Glu Pro Asp Ala Phe Asn
        275                 280                 285

Pro Cys Glu Asp Ile Met Gly Tyr Asp Phe Leu Arg Val Leu Ile Trp
    290                 295                 300

Leu Ile Asn Ile Leu Ala Ile Met Gly Asn Met Thr Val Leu Phe Val
305                 310                 315                 320

Leu Leu Thr Ser Arg Tyr Lys Leu Thr Val Pro Arg Phe Leu Met Cys
                325                 330                 335

Asn Leu Ser Phe Ala Asp Phe Cys Met Gly Leu Tyr Leu Leu Leu Ile
            340                 345                 350

Ala Ser Val Asp Ser Gln Thr Lys Gly Gln Tyr Tyr Asn His Ala Ile
        355                 360                 365

Asp Trp Gln Thr Gly Ser Gly Cys Ser Thr Ala Gly Phe Phe Thr Val
    370                 375                 380

Phe Ala Ser Glu Leu Ser Val Tyr Thr Leu Thr Val Ile Thr Leu Glu
385                 390                 395                 400

Arg Trp His Thr Ile Thr Tyr Ala Ile His Leu Asp Gln Lys Leu Arg
                405                 410                 415

Leu Arg His Ala Ile Leu Ile Met Leu Gly Gly Trp Leu Phe Ser Ser
            420                 425                 430

Leu Ile Ala Met Leu Pro Leu Val Gly Val Ser Asn Tyr Met Lys Val
        435                 440                 445

Ser Ile Cys Phe Pro Met Asp Val Glu Thr Thr Leu Ser Gln Val Tyr
    450                 455                 460

Ile Leu Thr Ile Leu Ile Leu Asn Val Val Ala Phe Phe Ile Ile Cys
465                 470                 475                 480

Ala Cys Tyr Ile Lys Ile Tyr Phe Ala Val Arg Asn Pro Glu Leu Met
                485                 490                 495

Ala Thr Asn Lys Asp Thr Lys Ile Ala Lys Lys Met Ala Ile Leu Ile
            500                 505                 510

Phe Thr Asp Phe Thr Cys Met Ala Pro Ile Ser Phe Phe Ala Ile Ser
        515                 520                 525

Ala Ala Phe Lys Val Pro Leu Ile Thr Val Thr Asn Ser Lys Val Leu
    530                 535                 540

Leu Val Leu Phe Tyr Pro Ile Asn Ser Cys Ala Asn Pro Phe Leu Tyr
545                 550                 555                 560

Ala Ile Phe Thr Lys Thr Phe Gln Arg Asp Phe Phe Leu Leu Leu Ser
                565                 570                 575

Lys Phe Gly Cys Cys Lys Arg Arg Ala Glu Leu Tyr Arg Arg Lys Asp
            580                 585                 590
```

-continued

```
Phe Ser Ala Tyr Thr Ser Asn Cys Lys Asn Gly Phe Thr Gly Ser Asn
        595                 600                 605

Lys Pro Ser Gln Ser Thr Leu Lys Leu Ser Thr Leu His Cys Gln Gly
    610                 615                 620

Thr Ala Leu Leu Asp Lys Thr Arg Tyr Thr Glu Cys
625                 630                 635


<210> SEQ ID NO 8
<211> LENGTH: 611
<212> TYPE: PRT
<213> ORGANISM: Homo sapiens

<400> SEQUENCE: 8

Arg Glu Ala Leu Cys Pro Glu Pro Cys Asn Cys Val Pro Asp Gly Ala
  1               5                  10                  15

Leu Arg Cys Pro Gly Pro Thr Ala Gly Leu Thr Arg Leu Ser Leu Ala
             20                  25                  30

Tyr Leu Pro Val Lys Val Ile Pro Ser Gln Ala Phe Arg Gly Leu Asn
         35                  40                  45

Glu Val Ile Lys Ile Glu Ile Ser Gln Ile Asp Ser Leu Glu Arg Ile
     50                  55                  60

Glu Ala Asn Ala Phe Asp Asn Leu Leu Asn Leu Ser Glu Ile Leu Ile
 65                  70                  75                  80

Gln Asn Thr Lys Asn Leu Arg Tyr Ile Glu Pro Gly Ala Phe Ile Asn
                 85                  90                  95

Leu Pro Gly Leu Lys Tyr Leu Ser Ile Cys Asn Thr Gly Ile Arg Lys
            100                 105                 110

Phe Pro Asp Val Thr Lys Val Phe Ser Ser Glu Ser Asn Phe Ile Leu
        115                 120                 125

Glu Ile Cys Asp Asn Leu His Ile Thr Thr Ile Pro Gly Asn Ala Phe
    130                 135                 140

Gln Gly Met Asn Asn Glu Ser Val Thr Leu Lys Leu Tyr Gly Asn Gly
145                 150                 155                 160

Phe Glu Glu Val Gln Ser His Ala Phe Asn Gly Thr Thr Leu Thr Ser
                165                 170                 175

Leu Glu Leu Lys Glu Asn Val His Leu Glu Lys Met His Asn Gly Ala
            180                 185                 190

Phe Arg Gly Ala Thr Gly Pro Lys Thr Gln Asn Phe Ser His Ser Ile
        195                 200                 205

Ser Glu Asn Phe Ser Lys Gln Cys Glu Ser Thr Val Arg Lys Val Ser
    210                 215                 220

Asn Lys Thr Leu Tyr Ser Ser Met Leu Ala Glu Ser Glu Leu Ser Gly
225                 230                 235                 240

Trp Asp Tyr Glu Tyr Gly Phe Cys Leu Pro Lys Thr Pro Arg Cys Ala
                245                 250                 255

Pro Glu Pro Asp Ala Phe Asn Pro Cys Glu Asp Ile Met Gly Tyr Asp
            260                 265                 270

Phe Leu Arg Val Leu Ile Trp Leu Ile Asn Ile Leu Ala Ile Met Gly
        275                 280                 285

Asn Met Thr Val Leu Phe Val Leu Leu Thr Ser Arg Tyr Lys Leu Thr
    290                 295                 300

Val Pro Arg Phe Leu Met Cys Asn Leu Ser Phe Ala Asp Phe Cys Met
305                 310                 315                 320

Gly Leu Tyr Leu Leu Leu Ile Ala Ser Val Asp Ser Gln Thr Lys Gly
```

-continued

```
            325                 330                 335

Gln Tyr Tyr Asn His Ala Ile Asp Trp Gln Thr Gly Ser Gly Cys Ser
            340                 345                 350

Thr Ala Gly Phe Phe Thr Val Phe Ala Ser Glu Leu Ser Val Tyr Thr
        355                 360                 365

Leu Thr Val Ile Thr Leu Glu Arg Trp His Thr Ile Thr Tyr Ala Ile
    370                 375                 380

His Leu Asp Gln Lys Leu Arg Leu Arg His Ala Ile Leu Ile Met Leu
385                 390                 395                 400

Gly Gly Trp Leu Phe Ser Ser Leu Ile Ala Met Leu Pro Leu Val Gly
                405                 410                 415

Val Ser Asn Tyr Met Lys Val Ser Ile Cys Phe Pro Met Asp Val Glu
            420                 425                 430

Thr Thr Leu Ser Gln Val Tyr Ile Leu Thr Ile Leu Ile Leu Asn Val
        435                 440                 445

Val Ala Phe Phe Ile Ile Cys Ala Cys Tyr Ile Lys Ile Tyr Phe Ala
    450                 455                 460

Val Arg Asn Pro Glu Leu Met Ala Thr Asn Lys Asp Thr Lys Ile Ala
465                 470                 475                 480

Lys Lys Met Ala Ile Leu Ile Phe Thr Asp Phe Thr Cys Met Ala Pro
                485                 490                 495

Ile Ser Phe Phe Ala Ile Ser Ala Ala Phe Lys Val Pro Leu Ile Thr
            500                 505                 510

Val Thr Asn Ser Lys Val Leu Leu Val Leu Phe Tyr Pro Ile Asn Ser
        515                 520                 525

Cys Ala Asn Pro Phe Leu Tyr Ala Ile Phe Thr Lys Thr Phe Gln Arg
    530                 535                 540

Asp Phe Phe Leu Leu Leu Ser Lys Phe Gly Cys Cys Lys Arg Arg Ala
545                 550                 555                 560

Glu Leu Tyr Arg Arg Lys Asp Phe Ser Ala Tyr Thr Ser Asn Cys Lys
                565                 570                 575

Asn Gly Phe Thr Gly Ser Asn Lys Pro Ser Gln Ser Thr Leu Lys Leu
            580                 585                 590

Ser Thr Leu His Cys Gln Gly Thr Ala Leu Leu Asp Lys Thr Arg Tyr
        595                 600                 605

Thr Glu Cys
    610


<210> SEQ ID NO 9
<211> LENGTH: 2022
<212> TYPE: DNA
<213> ORGANISM: Homo sapiens
<220> FEATURE:
<221> NAME/KEY: CDS
<222> LOCATION: (1)..(2022)

<400> SEQUENCE: 9

cgc gag gcg ctc tgc cct gag ccc tgc aac tgc gtg ccc gac ggc gcc       48
Arg Glu Ala Leu Cys Pro Glu Pro Cys Asn Cys Val Pro Asp Gly Ala
  1               5                  10                  15

ctg cgc tgc ccc ggc ccc acg gcc ggt ctc act cga cta tca ctt gcc       96
Leu Arg Cys Pro Gly Pro Thr Ala Gly Leu Thr Arg Leu Ser Leu Ala
            20                  25                  30

tac ctc cct gtc aaa gtg atc cca tct caa gct ttc aga gga ctt aat      144
Tyr Leu Pro Val Lys Val Ile Pro Ser Gln Ala Phe Arg Gly Leu Asn
         35                  40                  45
```

-continued

```
gag gtc ata aaa att gaa atc tct cag att gat tcc ctg gaa agg ata      192
Glu Val Ile Lys Ile Glu Ile Ser Gln Ile Asp Ser Leu Glu Arg Ile
     50                  55                  60

gaa gct aat gcc ttt gac aac ctc ctc aat ttg tct gaa ata ctg atc      240
Glu Ala Asn Ala Phe Asp Asn Leu Leu Asn Leu Ser Glu Ile Leu Ile
 65                  70                  75                  80

cag aac acc aaa aat ctg aga tac att gag ccc gga gca ttt ata aat      288
Gln Asn Thr Lys Asn Leu Arg Tyr Ile Glu Pro Gly Ala Phe Ile Asn
                 85                  90                  95

ctt ccc gga tta aaa tac ttg agc atc tgt aac aca ggc atc aga aag      336
Leu Pro Gly Leu Lys Tyr Leu Ser Ile Cys Asn Thr Gly Ile Arg Lys
            100                 105                 110

ttt cca gat gtt acg aag gtc ttc tcc tct gaa tca aat ttc att ctg      384
Phe Pro Asp Val Thr Lys Val Phe Ser Ser Glu Ser Asn Phe Ile Leu
        115                 120                 125

gaa att tgt gat aac tta cac ata acc acc ata cca gga aat gct ttt      432
Glu Ile Cys Asp Asn Leu His Ile Thr Thr Ile Pro Gly Asn Ala Phe
    130                 135                 140

caa ggg atg aat aat gaa tct gta aca ctc aaa cta tat gga aat gga      480
Gln Gly Met Asn Asn Glu Ser Val Thr Leu Lys Leu Tyr Gly Asn Gly
145                 150                 155                 160

ttt gaa gaa gta caa agt cat gca ttc aat ggg acg aca ctg act tca      528
Phe Glu Glu Val Gln Ser His Ala Phe Asn Gly Thr Thr Leu Thr Ser
                165                 170                 175

ctg gag cta aag gaa aac gta cat ctg gag aag atg cac aat gga gcc      576
Leu Glu Leu Lys Glu Asn Val His Leu Glu Lys Met His Asn Gly Ala
            180                 185                 190

ttc cgt ggg gcc aca ggg ccg aaa acc ttg gat att tct tcc acc aaa      624
Phe Arg Gly Ala Thr Gly Pro Lys Thr Leu Asp Ile Ser Ser Thr Lys
        195                 200                 205

ttg cag gcc ctg ccg agc tat ggc cta gag tcc att cag agg cta att      672
Leu Gln Ala Leu Pro Ser Tyr Gly Leu Glu Ser Ile Gln Arg Leu Ile
    210                 215                 220

gcc acg tca tcc tat tct cta aaa aaa ttg cca tca aga gaa aca ttt      720
Ala Thr Ser Ser Tyr Ser Leu Lys Lys Leu Pro Ser Arg Glu Thr Phe
225                 230                 235                 240

gtc aat ctc ctg gag gcc acg ttg act tac ccc agc cac tgc tgt gct      768
Val Asn Leu Leu Glu Ala Thr Leu Thr Tyr Pro Ser His Cys Cys Ala
                245                 250                 255

ttt aga aac ttg cca aca aaa gaa cag aat ttt tca cat tcc att tct      816
Phe Arg Asn Leu Pro Thr Lys Glu Gln Asn Phe Ser His Ser Ile Ser
            260                 265                 270

gaa aac ttt tcc aaa caa tgt gaa agc aca gta agg aaa gtg agt aac      864
Glu Asn Phe Ser Lys Gln Cys Glu Ser Thr Val Arg Lys Val Ser Asn
        275                 280                 285

aaa aca ctt tat tct tcc atg ctt gct gag agt gaa ctg agt ggc tgg      912
Lys Thr Leu Tyr Ser Ser Met Leu Ala Glu Ser Glu Leu Ser Gly Trp
    290                 295                 300

gac tat gaa tat ggt ttc tgc tta ccc aag aca ccc cga tgt gct cct      960
Asp Tyr Glu Tyr Gly Phe Cys Leu Pro Lys Thr Pro Arg Cys Ala Pro
305                 310                 315                 320

gaa cca gat gct ttt aat ccc tgt gaa gac att atg ggc tat gac ttc     1008
Glu Pro Asp Ala Phe Asn Pro Cys Glu Asp Ile Met Gly Tyr Asp Phe
                325                 330                 335

ctt agg gtc ctg att tgg ctg att aat att cta gcc atc atg gga aac     1056
Leu Arg Val Leu Ile Trp Leu Ile Asn Ile Leu Ala Ile Met Gly Asn
            340                 345                 350

atg act gtt ctt ttt gtt ctc ctg aca agt cgt tac aaa ctt aca gtg     1104
Met Thr Val Leu Phe Val Leu Leu Thr Ser Arg Tyr Lys Leu Thr Val
        355                 360                 365
```

-continued

```
cct cgt ttt ctc atg tgc aat ctc tcc ttt gca gac ttt tgc atg ggg     1152
Pro Arg Phe Leu Met Cys Asn Leu Ser Phe Ala Asp Phe Cys Met Gly
    370                 375                 380

ctc tat ctg ctg ctc ata gcc tca gtt gat tcc caa acc aag ggc cag     1200
Leu Tyr Leu Leu Leu Ile Ala Ser Val Asp Ser Gln Thr Lys Gly Gln
385                 390                 395                 400

tac tat aac cat gcc ata gac tgg cag aca ggg agt ggg tgc agc act     1248
Tyr Tyr Asn His Ala Ile Asp Trp Gln Thr Gly Ser Gly Cys Ser Thr
                405                 410                 415

gct ggc ttt ttc act gta ttc gca agt gaa ctt tct gtc tac acc ctc     1296
Ala Gly Phe Phe Thr Val Phe Ala Ser Glu Leu Ser Val Tyr Thr Leu
            420                 425                 430

acc gtc atc act cta gaa aga tgg cac acc atc acc tat gct att cac     1344
Thr Val Ile Thr Leu Glu Arg Trp His Thr Ile Thr Tyr Ala Ile His
        435                 440                 445

ctg gac caa aag ctg cga tta aga cat gcc att ctg att atg ctt gga     1392
Leu Asp Gln Lys Leu Arg Leu Arg His Ala Ile Leu Ile Met Leu Gly
    450                 455                 460

gga tgg ctc ttt tct tct cta att gct atg ttg ccc ctt gtc ggt gtc     1440
Gly Trp Leu Phe Ser Ser Leu Ile Ala Met Leu Pro Leu Val Gly Val
465                 470                 475                 480

agc aat tac atg aag gtc agt att tgc ttc ccc atg gat gtg gaa acc     1488
Ser Asn Tyr Met Lys Val Ser Ile Cys Phe Pro Met Asp Val Glu Thr
                485                 490                 495

act ctc tca caa gtc tat ata tta acc atc ctg att ctc aat gtg gtg     1536
Thr Leu Ser Gln Val Tyr Ile Leu Thr Ile Leu Ile Leu Asn Val Val
            500                 505                 510

gcc ttc ttc ata att tgt gct tgc tac att aaa att tat ttt gca gtt     1584
Ala Phe Phe Ile Ile Cys Ala Cys Tyr Ile Lys Ile Tyr Phe Ala Val
        515                 520                 525

cga aac cca gaa tta atg gct acc aat aaa gat aca aag att gct aag     1632
Arg Asn Pro Glu Leu Met Ala Thr Asn Lys Asp Thr Lys Ile Ala Lys
    530                 535                 540

aaa atg gca atc ctc atc ttc acc gat ttc acc tgc atg gca cct atc     1680
Lys Met Ala Ile Leu Ile Phe Thr Asp Phe Thr Cys Met Ala Pro Ile
545                 550                 555                 560

tct ttt ttt gcc atc tca gct gcc ttc aaa gta cct ctt atc aca gta     1728
Ser Phe Phe Ala Ile Ser Ala Ala Phe Lys Val Pro Leu Ile Thr Val
                565                 570                 575

acc aac tct aaa gtt tta ctg gtt ctt ttt tat ccc atc aat tct tgt     1776
Thr Asn Ser Lys Val Leu Leu Val Leu Phe Tyr Pro Ile Asn Ser Cys
            580                 585                 590

gcc aat cca ttt ctg tat gca ata ttc act aag aca ttc caa aga gat     1824
Ala Asn Pro Phe Leu Tyr Ala Ile Phe Thr Lys Thr Phe Gln Arg Asp
        595                 600                 605

ttc ttt ctt ttg ctg agc aaa ttt ggc tgc tgt aaa cgt cgg gct gaa     1872
Phe Phe Leu Leu Leu Ser Lys Phe Gly Cys Cys Lys Arg Arg Ala Glu
    610                 615                 620

ctt tat aga agg aaa gat ttt tca gct tac acc tcc aac tgc aaa aat     1920
Leu Tyr Arg Arg Lys Asp Phe Ser Ala Tyr Thr Ser Asn Cys Lys Asn
625                 630                 635                 640

ggc ttc act gga tca aat aag cct tct caa tcc acc ttg aag ttg tcc     1968
Gly Phe Thr Gly Ser Asn Lys Pro Ser Gln Ser Thr Leu Lys Leu Ser
                645                 650                 655

aca ttg cac tgt caa ggt aca gct ctc cta gac aag act cgc tac aca     2016
Thr Leu His Cys Gln Gly Thr Ala Leu Leu Asp Lys Thr Arg Tyr Thr
            660                 665                 670

gag tgt                                                             2022
Glu Cys
```

<210> SEQ ID NO 10
<211> LENGTH: 674
<212> TYPE: PRT
<213> ORGANISM: Homo sapiens

<400> SEQUENCE: 10

```
Arg Glu Ala Leu Cys Pro Glu Pro Cys Asn Cys Val Pro Asp Gly Ala
  1               5                  10                  15

Leu Arg Cys Pro Gly Pro Thr Ala Gly Leu Thr Arg Leu Ser Leu Ala
             20                  25                  30

Tyr Leu Pro Val Lys Val Ile Pro Ser Gln Ala Phe Arg Gly Leu Asn
         35                  40                  45

Glu Val Ile Lys Ile Glu Ile Ser Gln Ile Asp Ser Leu Glu Arg Ile
     50                  55                  60

Glu Ala Asn Ala Phe Asp Asn Leu Leu Asn Leu Ser Glu Ile Leu Ile
 65                  70                  75                  80

Gln Asn Thr Lys Asn Leu Arg Tyr Ile Glu Pro Gly Ala Phe Ile Asn
                 85                  90                  95

Leu Pro Gly Leu Lys Tyr Leu Ser Ile Cys Asn Thr Gly Ile Arg Lys
            100                 105                 110

Phe Pro Asp Val Thr Lys Val Phe Ser Ser Glu Ser Asn Phe Ile Leu
        115                 120                 125

Glu Ile Cys Asp Asn Leu His Ile Thr Thr Ile Pro Gly Asn Ala Phe
    130                 135                 140

Gln Gly Met Asn Asn Glu Ser Val Thr Leu Lys Leu Tyr Gly Asn Gly
145                 150                 155                 160

Phe Glu Glu Val Gln Ser His Ala Phe Asn Gly Thr Thr Leu Thr Ser
                165                 170                 175

Leu Glu Leu Lys Glu Asn Val His Leu Glu Lys Met His Asn Gly Ala
            180                 185                 190

Phe Arg Gly Ala Thr Gly Pro Lys Thr Leu Asp Ile Ser Ser Thr Lys
        195                 200                 205

Leu Gln Ala Leu Pro Ser Tyr Gly Leu Glu Ser Ile Gln Arg Leu Ile
    210                 215                 220

Ala Thr Ser Ser Tyr Ser Leu Lys Lys Leu Pro Ser Arg Glu Thr Phe
225                 230                 235                 240

Val Asn Leu Leu Glu Ala Thr Leu Thr Tyr Pro Ser His Cys Cys Ala
                245                 250                 255

Phe Arg Asn Leu Pro Thr Lys Glu Gln Asn Phe Ser His Ser Ile Ser
            260                 265                 270

Glu Asn Phe Ser Lys Gln Cys Glu Ser Thr Val Arg Lys Val Ser Asn
        275                 280                 285

Lys Thr Leu Tyr Ser Ser Met Leu Ala Glu Ser Glu Leu Ser Gly Trp
    290                 295                 300

Asp Tyr Glu Tyr Gly Phe Cys Leu Pro Lys Thr Pro Arg Cys Ala Pro
305                 310                 315                 320

Glu Pro Asp Ala Phe Asn Pro Cys Glu Asp Ile Met Gly Tyr Asp Phe
                325                 330                 335

Leu Arg Val Leu Ile Trp Leu Ile Asn Ile Leu Ala Ile Met Gly Asn
            340                 345                 350

Met Thr Val Leu Phe Val Leu Leu Thr Ser Arg Tyr Lys Leu Thr Val
        355                 360                 365

Pro Arg Phe Leu Met Cys Asn Leu Ser Phe Ala Asp Phe Cys Met Gly
```

-continued

```
    370                 375                 380

Leu Tyr Leu Leu Leu Ile Ala Ser Val Asp Ser Gln Thr Lys Gly Gln
385                 390                 395                 400

Tyr Tyr Asn His Ala Ile Asp Trp Gln Thr Gly Ser Gly Cys Ser Thr
                405                 410                 415

Ala Gly Phe Phe Thr Val Phe Ala Ser Glu Leu Ser Val Tyr Thr Leu
            420                 425                 430

Thr Val Ile Thr Leu Glu Arg Trp His Thr Ile Thr Tyr Ala Ile His
        435                 440                 445

Leu Asp Gln Lys Leu Arg Leu Arg His Ala Ile Leu Ile Met Leu Gly
    450                 455                 460

Gly Trp Leu Phe Ser Ser Leu Ile Ala Met Leu Pro Leu Val Gly Val
465                 470                 475                 480

Ser Asn Tyr Met Lys Val Ser Ile Cys Phe Pro Met Asp Val Glu Thr
                485                 490                 495

Thr Leu Ser Gln Val Tyr Ile Leu Thr Ile Leu Ile Leu Asn Val Val
            500                 505                 510

Ala Phe Phe Ile Ile Cys Ala Cys Tyr Ile Lys Ile Tyr Phe Ala Val
        515                 520                 525

Arg Asn Pro Glu Leu Met Ala Thr Asn Lys Asp Thr Lys Ile Ala Lys
    530                 535                 540

Lys Met Ala Ile Leu Ile Phe Thr Asp Phe Thr Cys Met Ala Pro Ile
545                 550                 555                 560

Ser Phe Phe Ala Ile Ser Ala Ala Phe Lys Val Pro Leu Ile Thr Val
                565                 570                 575

Thr Asn Ser Lys Val Leu Leu Val Leu Phe Tyr Pro Ile Asn Ser Cys
            580                 585                 590

Ala Asn Pro Phe Leu Tyr Ala Ile Phe Thr Lys Thr Phe Gln Arg Asp
        595                 600                 605

Phe Phe Leu Leu Leu Ser Lys Phe Gly Cys Cys Lys Arg Arg Ala Glu
    610                 615                 620

Leu Tyr Arg Arg Lys Asp Phe Ser Ala Tyr Thr Ser Asn Cys Lys Asn
625                 630                 635                 640

Gly Phe Thr Gly Ser Asn Lys Pro Ser Gln Ser Thr Leu Lys Leu Ser
                645                 650                 655

Thr Leu His Cys Gln Gly Thr Ala Leu Leu Asp Lys Thr Arg Tyr Thr
            660                 665                 670

Glu Cys


<210> SEQ ID NO 11
<211> LENGTH: 2799
<212> TYPE: DNA
<213> ORGANISM: Homo sapiens

<400> SEQUENCE: 11

atgaagcagc ggttctcggc gctgcagctg ctgaagctgc tgctgctgct gcagccgccg      60

ctgccacgag cgctgcgcga ggcgctctgc cctgagccct gcaactgcgt gcccgacggc     120

gccctgcgct gccccggccc cacggccggt ctcactcgac tatcacttgc ctacctccct     180

gtcaaagtga tcccatctca agctttcaga ggacttaatg aggtcataaa aattgaaatc     240

tctcagattg attccctgga aaggatagaa gctaatgcct ttgacaacct cctcaatttg     300

tctgaaatac tgatccagaa caccaaaaat ctgagataca ttgagcccgg agcatttata     360

aatcttcccg gattaaaata cttgagcatc tgtaacacag gcatcagaaa gtttccagat     420
```

-continued

```
gttacgaagg tcttctcctc tgaatcaaat ttcattctgg aaatttgtga taacttacac    480
ataaccacca taccaggaaa tgcttttcaa gggatgaata atgaatctgt aacactcaaa    540
ctatatggaa atggatttga agaagtacaa agtcatgcat tcaatgggac gacactgact    600
tcactggagc taaaggaaaa cgtacatctg gagaagatgc acaatggagc cttccgtggg    660
gccacagggc cgaaaaccac agaatttttc acattccatt tctgaaaact tttccaaaca    720
atgtgaaagc acagtaagga aagtgagtaa caaaacactt tattcttcca tgcttgctga    780
gagtgaactg agtggctggg actatgaata tggtttctgc ttacccaaga caccccgatg    840
tgctcctgaa ccagatgctt ttaatccctg tgaagacatt atgggctatg acttccttag    900
ggtcctgatt tggctgatta atattctagc catcatggga aacatgactg ttctttttgt    960
tctcctgaca agtcgttaca aacttacagt gcctcgtttt ctcatgtgca atctctcctt   1020
tgcagacttt tgcatggggc tctatctgct gctcatagcc tcagttgatt cccaaaccaa   1080
gggccagtac tataaccatg ccatagactg gcagacaggg agtgggtgca gcactgctgg   1140
ctttttcact gtattcgcaa gtgaactttc tgtctacacc ctcaccgtca tcactctaga   1200
aagatggcac accatcacct atgctattca cctggaccaa aagctgcgat taagacatgc   1260
cattctgatt atgcttggag gatggctctt ttcttctcta attgctatgt tgccccttgt   1320
cggtgtcagc aattacatga aggtcagtat ttgcttcccc atggatgtgg aaaccactct   1380
ctcacaagtc tatatattaa ccatcctgat tctcaatgtg gtggccttct tcataatttg   1440
tgcttgctac attaaaattt attttgcagt tcgaaaccca gaattaatgg ctaccaataa   1500
agatacaaag attgctaaga aaatggcaat cctcatcttc accgatttca cctgcatggc   1560
acctatctct ttttttgcca tctcagctgc cttcaaagta cctcttatca cagtaaccaa   1620
ctctaaagtt ttactggttc ttttttatcc catcaattct tgtgccaatc catttctgta   1680
tgcaatattc actaagacat tccaaagaga tttctttctt ttgctgagca aatttggctg   1740
ctgtaaacgt cgggctgaac tttatagaag gaaagatttt tcagcttaca cctccaactg   1800
caaaaatggc ttcactggat caaataagcc ttctcaatcc accttgaagt tgtccacatt   1860
gcactgtcaa ggtacagctc tcctagacaa gactcgctac acagagtgtt aactgttaca   1920
tcagtaactg cattattgaa ttgttcttaa acctgtaaaa aaaaattacc tgtaccagta   1980
attttaacat aaagggttgg atttaggaaa ttatttattt ttaggtacat taggcaagag   2040
acctctacct agtagaaagt gtagtctatg accactgcca cacgtaaaaa ctatttgtca   2100
ttgttacatg gcataaatat gaagttgaga gtgtttagaa atttttatag aaattttgac   2160
acagtaattt tgtttgatga atctttttaaa aaacagagga ggtattttgc atatcttttt   2220
ttcattttcg taatttgtat tgcattctat aaaaatatta gttcataaca gatcagaaat   2280
ttaaaataag ggctttttc ctcaggtagt ttgaaaaaca cactctagag atgcactgtt   2340
caattcggta cgcactagcc acatgtggct aaattaaaat taaataaaat gagaaatgta   2400
gtttctcagt tgcactacgt ttcaagttct caatggctac gtcaagttct caatggctac   2460
gtgtgactag tgcttaccat actggacagc acagacacag aatattttca tcaccacaga   2520
aagttctatc tgttctatta tagagacttt tatgtatgcc ctatctggat tctacttatt   2580
tataatttaa ggtaaacatc tgaaagcaca tttcagccta tttgcttagt gaaacattaa   2640
gctgtagact gtaaactcct cgtgagtagg aaccctgtct cagtgcattt tgttttcctg   2700
cttcctacct caagatcttg gcaatggtac actacaaatg tgctgagtta gaattactct   2760
```

-continued gaagttatga aacatataat gaaaacaatt tttccggcc 2799

<210> SEQ ID NO 12
<211> LENGTH: 2912
<212> TYPE: DNA
<213> ORGANISM: Homo sapiens

<400> SEQUENCE: 12
cgcgaggcgc tctgccctga gccctgcaac tgcgtgcccg acggcgccct gcgctgcccc 60
ggccccacgg ccggtctcac tcgactatca cttgcctacc tccctgtcaa agtgatccca 120
tctcaagctt tcagaggact taatgaggtc ataaaaattg aaatctctca gattgattcc 180
ctggaaagga tagaagctaa tgcctttgac aacctcctca atttgtctga aatactgatc 240
cagaacacca aaaatctgag atacattgag cccggagcat ttataaatct tcccggatta 300
aaatacttga gcatctgtaa cacaggcatc agaaagtttc cagatgttac gaaggtcttc 360
tcctctgaat caaatttcat tctggaaatt tgtgataact tacacataac caccatacca 420
ggaaatgctt ttcaagggat gaataatgaa tctgtaacac tcaaactata tggaaatgga 480
tttgaagaag tacaaagtca tgcattcaat gggacgacac tgacttcact ggagctaaag 540
gaaaacgtac atctggagaa gatgcacaat ggagccttcc gtggggccac agggccgaaa 600
accttggata tttcttccac caaattgcag gccctgccga gctatggcct agagtccatt 660
cagaggctaa ttgccacgtc atcctattct ctaaaaaaat tgccatcaag agaaacattt 720
gtcaatctcc tggaggccac gttgacttac cccagccact gctgtgcttt tagaaacttg 780
ccaacaaaag aacagaattt ttcacattcc atttctgaaa acttttccaa acaatgtgaa 840
agcacagtaa ggaaagtgag taacaaaaca ctttattctt ccatgcttgc tgagagtgaa 900
ctgagtggct gggactatga atatggtttc tgcttaccca agacaccccg atgtgctcct 960
gaaccagatg cttttaatcc ctgtgaagac attatgggct atgacttcct tagggtcctg 1020
atttggctga ttaatattct agccatcatg ggaaacatga ctgttctttt tgttctcctg 1080
acaagtcgtt acaaacttac agtgcctcgt tttctcatgt gcaatctctc ctttgcagac 1140
ttttgcatgg ggctctatct gctgctcata gcctcagttg attcccaaac caagggccag 1200
tactataacc atgccataga ctggcagaca gggagtgggt gcagcactgc tggctttttc 1260
actgtattcg caagtgaact ttctgtctac accctcaccg tcatcactct agaaagatgg 1320
cacaccatca cctatgctat tcacctggac caaaagctgc gattaagaca tgccattctg 1380
attatgcttg gaggatggct cttttcttct ctaattgcta tgttgcccct tgtcggtgtc 1440
agcaattaca tgaaggtcag tatttgcttc cccatggatg tggaaaccac tctctcacaa 1500
gtctatatat taaccatcct gattctcaat gtggtggcct tcttcataat ttgtgcttgc 1560
tacattaaaa tttattttgc agttcgaaac ccagaattaa tggctaccaa taaagataca 1620
aagattgcta agaaaatggc aatcctcatc ttcaccgatt tcacctgcat ggcacctatc 1680
tctttttttg ccatctcagc tgccttcaaa gtacctctta tcacagtaac caactctaaa 1740
gttttactgg ttcttttta tcccatcaat tcttgtgcca atccatttct gtatgcaata 1800
ttcactaaga cattccaaag agatttcttt cttttgctga gcaaatttgg ctgctgtaaa 1860
cgtcgggctg aactttatag aaggaaagat ttttcagctt acacctccaa ctgcaaaaat 1920
ggcttcactg gatcaaataa gccttctcaa tccaccttga agttgtccac attgcactgt 1980
caaggtacag ctctcctaga caagactcgc tacacagagt gttaactgtt acatcagtaa 2040
ctgcattatt gaattgttct taaacctgta aaaaaaaatt acctgtacca gtaattttaa 2100

-continued

```
cataaagggt tggatttagg aaattattta tttttaggta cattaggcaa gagacctcta   2160
cctagtagaa agtgtagtct atgaccactg ccacacgtaa aaactatttg tcattgttac   2220
atggcataaa tatgaagttg agagtgttta gaaattttta tagaaatttt gacacagtaa   2280
ttttgtttga tgaatctttt aaaaaacaga ggaggtattt tgcatatctt tttttcattt   2340
tcgtaatttg tattgcattc tataaaaata ttagttcata acagatcaga aatttaaaat   2400
aaggggcttt ttcctcaggt agtttgaaaa acacactcta gagatgcact gttcaattcg   2460
gtacgcacta gccacatgtg gctaaattaa aattaaataa aatgagaaat gtagtttctc   2520
agttgcacta cgtttcaagt tctcaatggc tacgtcaagt tctcaatggc tacgtgtgac   2580
tagtgcttac catactggac agcacagaca cagaatattt tcatcaccac agaaagttct   2640
atctgttcta ttatagagac ttttatgtat gccctatctg gattctactt atttataatt   2700
taaggtaaac atctgaaagc acatttcagc ctatttgctt agtgaaacat taagctgtag   2760
actgtaaact cctcgtgagt aggaaccctg tctcagtgca ttttgttttc ctgcttccta   2820
cctcaagatc ttggcaatgg tacactacaa atgtgctgag ttagaattac tctgaagtta   2880
tgaaacatat aatgaaaaca atttttccgg cc                                 2912
```

<210> SEQ ID NO 13
<211> LENGTH: 2724
<212> TYPE: DNA
<213> ORGANISM: Homo sapiens

<400> SEQUENCE: 13

```
cgcgaggcgc tctgccctga gccctgcaac tgcgtgcccg acggcgccct gcgctgcccc     60
ggccccacgg ccggtctcac tcgactatca cttgcctacc tccctgtcaa agtgatccca    120
tctcaagctt tcagaggact taatgaggtc ataaaaattg aaatctctca gattgattcc    180
ctggaaagga tagaagctaa tgcctttgac aacctcctca atttgtctga aatactgatc    240
cagaacacca aaaatctgag atacattgag cccggagcat ttataaatct tcccggatta    300
aaatacttga gcatctgtaa cacaggcatc agaaagtttc cagatgttac gaaggtcttc    360
tcctctgaat caaatttcat tctggaaatt tgtgataact tacacataac caccatacca    420
ggaaatgctt ttcaagggat gaataatgaa tctgtaacac tcaaactata tggaaatgga    480
tttgaagaag tacaaagtca tgcattcaat gggacgacac tgacttcact ggagctaaag    540
gaaaacgtac atctggagaa gatgcacaat ggagccttcc gtggggccac agggccgaaa    600
accacagaat ttttcacatt ccatttctga aaacttttcc aaacaatgtg aaagcacagt    660
aaggaaagtg agtaacaaaa cactttattc ttccatgctt gctgagagtg aactgagtgg    720
ctgggactat gaatatggtt tctgcttacc caagacaccc cgatgtgctc ctgaaccaga    780
tgcttttaat ccctgtgaag acattatggg ctatgacttc cttagggtcc tgatttggct    840
gattaatatt ctagccatca tgggaaacat gactgttctt tttgttctcc tgacaagtcg    900
ttacaaactt acagtgcctc gttttctcat gtgcaatctc tcctttgcag acttttgcat    960
ggggctctat ctgctgctca tagcctcagt tgattcccaa accaagggcc agtactataa   1020
ccatgccata gactggcaga cagggagtgg gtgcagcact gctggctttt tcactgtatt   1080
cgcaagtgaa ctttctgtct acaccctcac cgtcatcact ctagaaagat ggcacaccat   1140
cacctatgct attcacctgg accaaaagct gcgattaaga catgccattc tgattatgct   1200
tggaggatgg ctcttttctt ctctaattgc tatgttgccc cttgtcggtg tcagcaatta   1260
```

-continued

```
catgaaggtc agtatttgct tccccatgga tgtggaaacc actctctcac aagtctatat   1320
attaaccatc ctgattctca atgtggtggc cttcttcata atttgtgctt gctacattaa   1380
aatttatttt gcagttcgaa acccagaatt aatggctacc aataaagata caaagattgc   1440
taagaaaatg gcaatcctca tcttcaccga tttcacctgc atggcaccta tctctttttt   1500
tgccatctca gctgccttca aagtacctct tatcacagta accaactcta aagttttact   1560
ggttctttttt tatcccatca attcttgtgc caatccattt ctgtatgcaa tattcactaa   1620
gacattccaa agagatttct ttcttttgct gagcaaattt ggctgctgta aacgtcgggc   1680
tgaactttat agaaggaaag atttttcagc ttacacctcc aactgcaaaa atggcttcac   1740
tggatcaaat aagccttctc aatccacctt gaagttgtcc acattgcact gtcaaggtac   1800
agctctccta gacaagactc gctacacaga gtgttaactg ttacatcagt aactgcatta   1860
ttgaattgtt cttaaacctg taaaaaaaaa ttacctgtac cagtaatttt aacataaagg   1920
gttggattta ggaaattatt tatttttagg tacattaggc aagagacctc tacctagtag   1980
aaagtgtagt ctatgaccac tgccacacgt aaaaactatt tgtcattgtt acatggcata   2040
aatatgaagt tgagagtgtt tagaaatttt tatagaaatt ttgacacagt aattttgttt   2100
gatgaatctt ttaaaaaaca gaggaggtat tttgcatatc ttttttttcat tttcgtaatt   2160
tgtattgcat tctataaaaa tattagttca taacagatca gaaatttaaa ataaggggct   2220
ttttcctcag gtagtttgaa aaacacactc tagagatgca ctgttcaatt cggtacgcac   2280
tagccacatg tggctaaatt aaaattaaat aaaatgagaa atgtagtttc tcagttgcac   2340
tacgtttcaa gttctcaatg gctacgtcaa gttctcaatg gctacgtgtg actagtgctt   2400
accatactgg acagcacaga cacagaatat tttcatcacc acagaaagtt ctatctgttc   2460
tattatagag acttttatgt atgccctatc tggattctac ttatttataa tttaaggtaa   2520
acatctgaaa gcacatttca gcctatttgc ttagtgaaac attaagctgt agactgtaaa   2580
ctcctcgtga gtaggaaccc tgtctcagtg cattttgttt tcctgcttcc tacctcaaga   2640
tcttggcaat ggtacactac aaatgtgctg agttagaatt actctgaagt tatgaaacat   2700
ataatgaaaa caatttttcc ggcc                                          2724
```

<210> SEQ ID NO 14
<211> LENGTH: 2097
<212> TYPE: DNA
<213> ORGANISM: Homo sapiens

<400> SEQUENCE: 14

```
atgaagcagc ggttctcggc gctgcagctg ctgaagctgc tgctgctgct gcagccgccg     60
ctgccacgag cgctgcgcga ggcgctctgc cctgagccct gcaactgcgt gcccgacggc    120
gccctgcgct gccccggccc cacggccggt ctcactcgac tatcacttgc ctacctccct    180
gtcaaagtga tcccatctca agctttcaga ggacttaatg aggtcataaa aattgaaatc    240
tctcagattg attccctgga aaggatagaa gctaatgcct ttgacaacct cctcaatttg    300
tctgaaatac tgatccagaa caccaaaaat ctgagataca ttgagcccgg agcatttata    360
aatcttcccg gattaaaata cttgagcatc tgtaacacag gcatcagaaa gtttccagat    420
gttacgaagg tcttctcctc tgaatcaaat ttcattctgg aaatttgtga taacttacac    480
ataaccacca taccaggaaa tgcttttcaa gggatgaata atgaatctgt aacactcaaa    540
ctatatggaa atggatttga agaagtacaa agtcatgcat tcaatgggac gacactgact    600
tcactggagc taaaggaaaa cgtacatctg gagaagatgc acaatggagc cttccgtggg    660
```

```
gccacagggc cgaaaacctt ggatatttct tccaccaaat tgcaggccct gccgagctat    720
ggcctagagt ccattcagag gctaattgcc acgtcatcct attctctaaa aaaattgcca    780
tcaagagaaa catttgtcaa tctcctggag gccacgttga cttaccccag ccactgctgt    840
gcttttagaa acttgccaac aaaagaacag aatttttcac attccatttc tgaaaacttt    900
tccaaacaat gtgaaagcac agtaaggaaa gtgagtaaca aaacacttta ttcttccatg    960
cttgctgaga gtgaactgag tggctgggac tatgaatatg gtttctgctt acccaagaca   1020
ccccgatgtg ctcctgaacc agatgctttt aatccctgtg aagacattat gggctatgac   1080
ttccttaggg tcctgatttg gctgattaat attctagcca tcatgggaaa catgactgtt   1140
ctttttgttc tcctgacaag tcgttacaaa cttacagtgc ctcgttttct catgtgcaat   1200
ctctcctttg cagacttttg catggggctc tatctgctgc tcatagcctc agttgattcc   1260
caaaccaagg gccagtacta taaccatgcc atagactggc agacagggag tgggtgcagc   1320
actgctggct tttcactgt  attcgcaagt gaactttctg tctacaccct caccgtcatc   1380
actctagaaa gatggcacac catcacctat gctattcacc tggaccaaaa gctgcgatta   1440
agacatgcca ttctgattat gcttggagga tggctctttt cttctctaat tgctatgttg   1500
ccccttgtcg gtgtcagcaa ttacatgaag gtcagtattt gcttccccat ggatgtggaa   1560
accactctct cacaagtcta tatattaacc atcctgattc tcaatgtggt ggccttcttc   1620
ataatttgtg cttgctacat taaaatttat tttgcagttc gaaacccaga attaatggct   1680
accaataaag atacaaagat tgctaagaaa atggcaatcc tcatcttcac cgatttcacc   1740
tgcatggcac ctatctcttt ttttgccatc tcagctgcct tcaaagtacc tcttatcaca   1800
gtaaccaact ctaaagtttt actggttctt ttttatccca tcaattcttg tgccaatcca   1860
tttctgtatg caatattcac taagacattc caaagagatt tctttctttt gctgagcaaa   1920
tttggctgct gtaaacgtcg ggctgaactt tatagaagga aagatttttc agcttacacc   1980
tccaactgca aaaatggctt cactggatca aataagcctt ctcaatccac cttgaagttg   2040
tccacattgc actgtcaagg tacagctctc ctagacaaga ctcgctacac agagtgt      2097
```

<210> SEQ ID NO 15
<211> LENGTH: 2022
<212> TYPE: DNA
<213> ORGANISM: Homo sapiens

<400> SEQUENCE: 15

```
cgcgaggcgc tctgccctga gccctgcaac tgcgtgcccg acggcgccct gcgctgcccc     60
ggccccacgg ccggtctcac tcgactatca cttgcctacc tccctgtcaa agtgatccca    120
tctcaagctt tcagaggact taatgaggtc ataaaaattg aaatctctca gattgattcc    180
ctggaaagga tagaagctaa tgcctttgac aacctcctca atttgtctga aatactgatc    240
cagaacacca aaaatctgag atacattgag cccggagcat ttataaatct tcccggatta    300
aaatacttga gcatctgtaa cacaggcatc agaaagtttc cagatgttac gaaggtcttc    360
tcctctgaat caaatttcat tctggaaatt tgtgataact tacacataac caccatacca    420
ggaaatgctt ttcaagggat gaataatgaa tctgtaacac tcaaactata tggaaatgga    480
tttgaagaag tacaaagtca tgcattcaat gggacgacac tgacttcact ggagctaaag    540
gaaaacgtac atctggagaa gatgcacaat ggagccttcc gtggggccac agggccgaaa    600
accttggata tttcttccac caaattgcag gccctgccga gctatggcct agagtccatt    660
```

-continued

```
cagaggctaa ttgccacgtc atcctattct ctaaaaaaat tgccatcaag agaaacattt    720
gtcaatctcc tggaggccac gttgacttac cccagccact gctgtgcttt tagaaacttg    780
ccaacaaaag aacagaattt ttcacattcc atttctgaaa acttttccaa acaatgtgaa    840
agcacagtaa ggaaagtgag taacaaaaca ctttattctt ccatgcttgc tgagagtgaa    900
ctgagtggct gggactatga atatggtttc tgcttaccca agacaccccg atgtgctcct    960
gaaccagatg cttttaatcc ctgtgaagac attatgggct atgacttcct tagggtcctg   1020
atttggctga ttaatattct agccatcatg ggaaacatga ctgttctttt tgttctcctg   1080
acaagtcgtt acaaacttac agtgcctcgt tttctcatgt gcaatctctc ctttgcagac   1140
ttttgcatgg ggctctatct gctgctcata gcctcagttg attcccaaac caagggccag   1200
tactataacc atgccataga ctggcagaca gggagtgggt gcagcactgc tggctttttc   1260
actgtattcg caagtgaact ttctgtctac accctcaccg tcatcactct agaaagatgg   1320
cacaccatca cctatgctat tcacctggac caaaagctgc gattaagaca tgccattctg   1380
attatgcttg gaggatggct cttttcttct ctaattgcta tgttgcccct tgtcggtgtc   1440
agcaattaca tgaaggtcag tatttgcttc cccatggatg tggaaaccac tctctcacaa   1500
gtctatatat taaccatcct gattctcaat gtggtggcct tcttcataat ttgtgcttgc   1560
tacattaaaa tttattttgc agttcgaaac ccagaattaa tggctaccaa taaagataca   1620
aagattgcta agaaaatggc aatcctcatc ttcaccgatt tcacctgcat ggcacctatc   1680
tctttttttg ccatctcagc tgccttcaaa gtacctctta tcacagtaac caactctaaa   1740
gttttactgg ttcttttttta tcccatcaat tcttgtgcca atccatttct gtatgcaata   1800
ttcactaaga cattccaaag agatttcttt cttttgctga gcaaatttgg ctgctgtaaa   1860
cgtcgggctg aactttatag aaggaaagat tttcagctt acacctccaa ctgcaaaaat   1920
ggcttcactg gatcaaataa gccttctcaa tccaccttga agttgtccac attgcactgt   1980
caaggtacag ctctcctaga caagactcgc tacacagagt gt                      2022
```

```
<210> SEQ ID NO 16
<211> LENGTH: 1909
<212> TYPE: DNA
<213> ORGANISM: Homo sapiens

<400> SEQUENCE: 16

atgaagcagc ggttctcggc gctgcagctg ctgaagctgc tgctgctgct gcagccgccg     60
ctgccacgag cgctgcgcga ggcgctctgc cctgagccct gcaactgcgt gcccgacggc    120
gccctgcgct gccccggccc cacggccggt ctcactcgac tatcacttgc ctacctccct    180
gtcaaagtga tcccatctca agctttcaga ggacttaatg aggtcataaa aattgaaatc    240
tctcagattg attccctgga aaggatagaa gctaatgcct ttgacaacct cctcaatttg    300
tctgaaatac tgatccagaa caccaaaaat ctgagataca ttgagcccgg agcatttata    360
aatcttcccg gattaaaata cttgagcatc tgtaacacag gcatcagaaa gtttccagat    420
gttacgaagg tcttctcctc tgaatcaaat ttcattctgg aaatttgtga taacttacac    480
ataaccacca taccaggaaa tgcttttcaa gggatgaata atgaatctgt aacactcaaa    540
ctatatggaa atggatttga agaagtacaa agtcatgcat tcaatgggac gacactgact    600
tcactggagc taaaggaaaa cgtacatctg gagaagatgc acaatggagc cttccgtggg    660
gccacagggc cgaaaaccac agaatttttc acattccatt tctgaaaact tttccaaaca    720
atgtgaaagc acagtaagga aagtgagtaa caaaacactt tattcttcca tgcttgctga    780
```

-continued

```
gagtgaactg agtggctggg actatgaata tggtttctgc ttacccaaga caccccgatg    840
tgctcctgaa ccagatgctt ttaatccctg tgaagacatt atgggctatg acttccttag    900
ggtcctgatt tggctgatta atattctagc catcatggga aacatgactg ttctttttgt    960
tctcctgaca agtcgttaca aacttacagt gcctcgtttt ctcatgtgca atctctcctt   1020
tgcagacttt tgcatggggc tctatctgct gctcatagcc tcagttgatt cccaaaccaa   1080
gggccagtac tataaccatg ccatagactg gcagacaggg agtgggtgca gcactgctgg   1140
ctttttcact gtattcgcaa gtgaactttc tgtctacacc ctcaccgtca tcactctaga   1200
aagatggcac accatcacct atgctattca cctggaccaa aagctgcgat taagacatgc   1260
cattctgatt atgcttggag gatggctctt ttcttctcta attgctatgt tgccccttgt   1320
cggtgtcagc aattacatga aggtcagtat ttgcttcccc atggatgtgg aaaccactct   1380
ctcacaagtc tatatattaa ccatcctgat tctcaatgtg gtggccttct tcataatttg   1440
tgcttgctac attaaaattt attttgcagt tcgaaaccca gaattaatgg ctaccaataa   1500
agatacaaag attgctaaga aaatggcaat cctcatcttc accgatttca cctgcatggc   1560
acctatctct ttttttgcca tctcagctgc cttcaaagta cctcttatca cagtaaccaa   1620
ctctaaagtt ttactggttc tttttatcc catcaattct tgtgccaatc catttctgta   1680
tgcaatattc actaagacat tccaaagaga tttctttctt ttgctgagca aatttggctg   1740
ctgtaaacgt cgggctgaac tttatagaag gaaagatttt tcagcttaca cctccaactg   1800
caaaaatggc ttcactggat caaataagcc ttctcaatcc accttgaagt tgtccacatt   1860
gcactgtcaa ggtacagctc tcctagacaa gactcgctac acagagtgt               1909
```

<210> SEQ ID NO 17
<211> LENGTH: 1834
<212> TYPE: DNA
<213> ORGANISM: Homo sapiens

<400> SEQUENCE: 17

```
cgcgaggcgc tctgccctga gccctgcaac tgcgtgcccg acggcgccct gcgctgcccc     60
ggccccacgg ccggtctcac tcgactatca cttgcctacc tccctgtcaa agtgatccca    120
tctcaagctt tcagaggact taatgaggtc ataaaaattg aaatctctca gattgattcc    180
ctggaaagga tagaagctaa tgcctttgac aacctcctca atttgtctga aatactgatc    240
cagaacacca aaaatctgag atacattgag cccggagcat ttataaatct tcccggatta    300
aaatacttga gcatctgtaa cacaggcatc agaaagtttc cagatgttac gaaggtcttc    360
tcctctgaat caaatttcat tctggaaatt tgtgataact tacacataac caccatacca    420
ggaaatgctt ttcaagggat gaataatgaa tctgtaacac tcaaactata tggaaatgga    480
tttgaagaag tacaaagtca tgcattcaat gggacgacac tgacttcact ggagctaaag    540
gaaaacgtac atctggagaa gatgcacaat ggagccttcc gtggggccac agggccgaaa    600
accacagaat tttcacatt ccatttctga aaacttttcc aaacaatgtg aaagcacagt    660
aaggaaagtg agtaacaaaa cactttattc ttccatgctt gctgagagtg aactgagtgg    720
ctgggactat gaatatggtt tctgcttacc caagacaccc cgatgtgctc ctgaaccaga    780
tgcttttaat ccctgtgaag acattatggg ctatgacttc cttagggtcc tgatttggct    840
gattaatatt ctagccatca tgggaaacat gactgttctt tttgttctcc tgacaagtcg    900
ttacaaactt acagtgcctc gttttctcat gtgcaatctc tcctttgcag acttttgcat    960
```

-continued

```
ggggctctat ctgctgctca tagcctcagt tgattcccaa accaagggcc agtactataa   1020

ccatgccata gactggcaga cagggagtgg gtgcagcact gctggctttt tcactgtatt   1080

cgcaagtgaa ctttctgtct acaccctcac cgtcatcact ctagaaagat ggcacaccat   1140

cacctatgct attcacctgg accaaaagct gcgattaaga catgccattc tgattatgct   1200

tggaggatgg ctcttttctt ctctaattgc tatgttgccc cttgtcggtg tcagcaatta   1260

catgaaggtc agtatttgct tccccatgga tgtggaaacc actctctcac aagtctatat   1320

attaaccatc ctgattctca atgtggtggc cttcttcata atttgtgctt gctacattaa   1380

aatttatttt gcagttcgaa acccagaatt aatggctacc aataaagata caaagattgc   1440

taagaaaatg gcaatcctca tcttcaccga tttcacctgc atggcaccta tctctttttt   1500

tgccatctca gctgccttca aagtacctct tatcacagta accaactcta aagttttact   1560

ggttctttt tatcccatca attcttgtgc caatccattt ctgtatgcaa tattcactaa   1620

gacattccaa agagatttct ttcttttgct gagcaaattt ggctgctgta aacgtcgggc   1680

tgaactttat agaaggaaag atttttcagc ttacacctcc aactgcaaaa atggcttcac   1740

tggatcaaat aagccttctc aatccacctt gaagttgtcc acattgcact gtcaaggtac   1800

agctctccta gacaagactc gctacacaga gtgt                               1834
```

NUCLEIC ACID MOLECULES ENCODING HUMAN LUTEINIZING HORMONE-HUMAN CHORIONIC GONADOTROPIN RECEPTOR PROTEIN AND TRANSFORMANTS THEREOF

This application is a continuation of U.S. patent application Ser. No. 07/757,342, filed on Sep. 10, 1991, now U.S. Pat. No. 6,218,509.

BACKGROUND OF THE INVENTION

The present invention relates to a DNA containing a CDNA sequence coding for a human luteinizing hormone-human chorionic gonadotropin receptor protein (human LH/hCG receptor protein), the human LH/hCG receptor protein, and a method for preparing the protein.

The human luteinizing hormone-human chorionic gonadotropin receptor proteins (human LH/hCG receptor proteins) exist in the Leydig cells in the testis, the theca cells in the ovary, the granulosa cells, the corpus luteum cells and the interstitial cells, and play a central role in reproductive physiology. In the male and the female who is not pregnant, the LH/hCG receptor proteins are acted on only by luteinizing hormone (LH) produced in the anterior lobe of the pituitary and secreted therefrom. In the pregnant female, however, the LH/hCG receptor proteins in the ovary are acted on also by human chorionic gonadotropin (hCG) produced by the placenta.

LH and hCG are members of a family of glycoprotein hormones also including thyroid-stimulating hormone (TSH) and follicle-stimulating hormone (FSH). Each of these four hormones has a molecular weight of 28 to 38 kD, and is a heterodimer glycoprotein in which a specific β subunit relating to receptor binding specificity is bound to an a subunit common to these hormones. The glycosyl moiety of these hormones seem to play an important role in signal introduction. The β subunits of both LH and hCG are closely related to each other in their structure. These two hormones bind to the same receptor and induce the same biological reaction. The similarity between these glycoprotein hormones and the action by these hormones on the receptors to enhance the activity of adenylate cyclase mediated by G-proteins reveal that these receptors have a common mechanism of hormone-induced activation. The increases of adenosine 3',5'-monophosphate (cyclic AMP) necessarily lead to the synthesis and secretion of steroids. A family of G protein-coupled receptors are identified whose members are characterized by the common structural feature of having seven transmembrane domains which are known to relate to the signal introduction and binding to small ligands. On the other hand, TSH and FSH receptors have been compared with the LH/hCG receptors. As a result, of the G protein-coupled receptors, these receptors of the pituitary glycoprotein hormones are characterized by the presence of a large glycosylated domain which is grafted onto a structure containing seven transmembrane segments and putatively considered to be positioned on the outside of cells.

The structure of the LH/hCG receptors have not been elucidated so well yet, because the receptors are present in very low amounts and sensitive to proteolysis. For rat and porcine LH/hCG receptors, however, complementary DNAs (cDNAs) of these receptors are isolated and the amino acid sequences thereof are also deduced from these DNAs [*Science* 245, 494 (1989) for rats and *Science* 245, 525 (1989) for pigs].

For the rat and porcine LH/hCG receptors, the structure thereof has been thus elucidated. For the human LH/hCG receptors, however, the structure thereof is not revealed. Considering to use the human LH/hCG receptors as therapeutic drugs and analytical reagents for humans, it is necessary to make clear the structure and properties thereof.

SUMMARY OF THE INVENTION

The present inventors have recognized that important contributions will be made to future studies and medical treatments, if an human LH/hCG receptor can be collected from humans and further prepared by recombinant technology. As a result, the present inventors have first succeeded in cloning cDNA coding for a human LH/hCG receptor from a cDNA library of the human ovary by using the complementary DNA of a rat LH/hCG receptor as a probe, and in elucidating a complete nucleotide sequence thereof. Further, the present inventors have also succeeded in elucidating an amino acid sequence of the human LH/hCG receptor from this cDNA and in pioneering the mass production of this receptor by recombinant technology. This receptor is very similar to the rat and porcine receptors. However, the differences are such that each receptor can be recognized to be a different one.

In accordance with the present invention, there are provided (1) a human luteinizing hormone-human chorionic gonadotropin receptor protein, (2) a DNA comprising a cDNA sequence coding for a human luteinizing hormone-human chorionic gonadotropin receptor protein, (3) a transformant carrying a DNA comprising a cDNA segment coding for a human luteinizing hormone-human chorionic gonadotropin receptor protein, and (4) a method for preparing a human luteinizing hormone-human chorionic gonadotropin receptor protein which comprises culturing the transformant described in (3), accumulating a protein in a culture broth, and collecting the same.

BRIEF DESCRIPTION OF THE DRAWINGS

FIGS. A1–1E shows a nucleotide sequence SEQ ID NO:1 of a human LH/hCG receptor protein DNA segment, as well as an amino acid sequence SEQ ID NO:2 deduced therefrom; and FIGS. 2A–2D shows the amino acid sequence of the human LH/hCG receptor protein (SEQ ID NO:2) and amino acid sequences of other known LH/hCG receptor proteins and proteins (SEQ ID NOS:3 to 6) having similar action, comparing them to one another.

DESCRIPTION OF THE PREFERRED EMBODIMENTS

Figure 3:
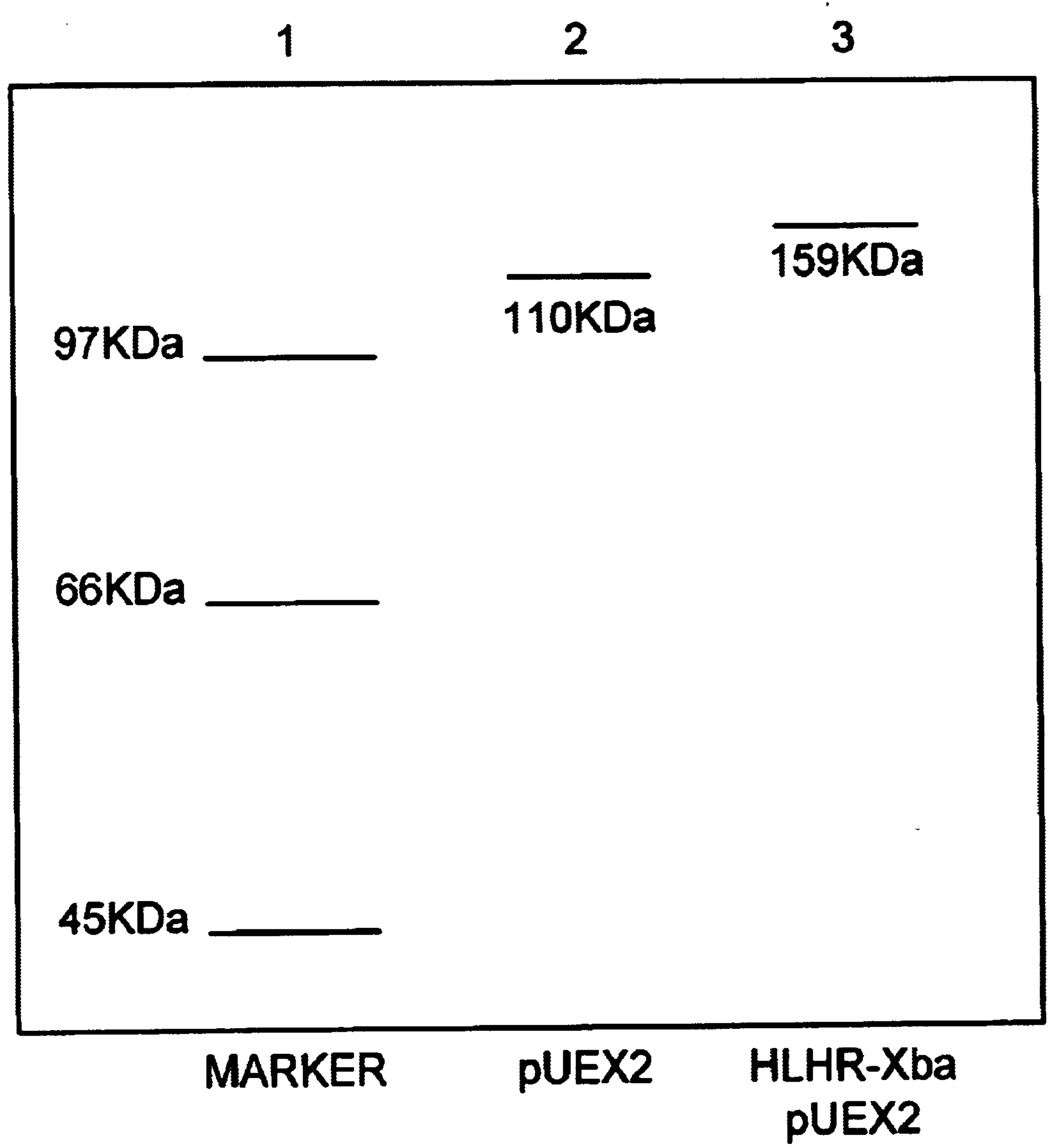
FIGS. 3 and 4 are SDS-PAGE diagrams which show expression of HLHR protein in Example 2.

The present inventors cloned two kinds of cDNAs of the human luteinizing hormone-human chorionic gonadotropin receptor protein to deduce a primary structure of the complete protein (FIGS. 1A–1E). The first methionine in this sequence SEQ ID NO:1 is considered to be an initiator codon. This is followed by an amino acid sequence having the characteristics of a signal peptide with a cleavage site present. A possible model for construction of the protein was suggested by hydropathy analysis and comparison with the rat and porcine LH/hCG receptors SEQ ID NO:3 and 4 respectively (FIGS. 2A–2D). A putative extracellular domain of 335 amino acids precedes a region of 267 amino acids that displays seven possible transmembrane segments (regions surrounded by rectangles in FIGS. 2A–2D). There is a 72 amino acid COOH-terminal intracellular domain. The mature protein may consist of 674 amino acids (75632 daltons). In addition to this protein, 25 signal peptides (the 1st to 25th amino acids in FIGS. 1A–1E and 2A–2D) exist.

However, these peptides are cut off during synthesis of the receptor, and therefore the mature protein of the receptor is considered to consist of 674 amino acids (the $26^{th}$ to $699^{th}$ amino acids, SEQ ID NO:10 is the amino acid sequence of SEQ ID NO:9. At the primary structure level, this extracellular domain has about 85% homology with the rat and porcine LH/hCG receptors and 45% homology with TSH and FSH receptors (in FIGS. 2A–2D, hLH/hCGR indicates the human LH/hCG receptor; rLH/hCGR indicates the rat LH/hCG receptor; pLH/hCGR indicates the porcine LH/hCG receptor; hTSHR indicates the human TSH receptor [*Biochem. Biophys. Res. Comm.* 166, 394 (1990)]; and rFSHR indicates the rat FSH receptor [*Mol. Endo.* 4, 525 (1990)]). Six potential glycosylation sites are found in the putative extracellular domain (underlined portions in FIGS. 1A–1E). Clusters of cysteine residues are present in the $NH_2$-terminal portion and between the putative extracellular and transmembrane domains of the above protein. Since these cysteine residues are conserved in the LH, FSH and TSH receptors, while not wishing to be bound by theory, it may be said that the formation of disulfide bonds is crucial for the conformational integrity of the large extracellular domains of glycoprotein hormone receptors.

The domain considered to contain the transmembrane domains has about 90% homology with the rat and porcine LH/hCG receptors, and 70% homology with the TSH and FSH receptors. Serine and threonine residues are found with high frequency in a putative intercellular domain having three sites which is possibly phosphorylated by protein kinase C (FIGS. 1A and 1E). Since the phosphorylation by protein kinase specific to the receptors play a role in agonist specific decoupling of adrenergic receptors from the G proteins, it is important to know whether the phosphorylation in at least one of these sites causes any functional changes of the LH/hCG receptors.

In the present invention, in addition to a clone having a large open reading frame, a clone coding for a shorter protein was obtained. The large clone is the 1st to 699th amono acid residues in FIGS. 1A–1E (SEQ ID NO:1), and the truncated-type is one from which a region of the 227th to 289th amino acid residue surrounded by a rectangle SEQ ID NO:7 is lacking. This pattern suggests that the cleavage mechanism necessary to complete mRNA has selectivity. These results are very similar to the data of the porcine LH/hCG receptor. The role of this truncated type receptor is not understood well, and it is not known either whether this LH/hCG receptor is physiologically active as a monomer or an oligomer. In humans, this TSH receptor can be a target of autoimmune reaction which leads to hyper- or hypo-stimulation of the thyroid gland by autoantibodies in Grave's disease and idiopathic myxedema. Thus, not only for contributions to diagnosis and management of ovarian diseases, but also for better understanding of ovarian physiology, it is necessary to isolate the human LH/hCG receptor and to know its characteristics.

FIGS. 2A–2D show the amino acid sequence of the novel human luteinizing hormone-human chorionic gonadotropin receptor protein SEQ ID NO:2 obtained in the present invention, and compares this amino acid sequence with the amino acid sequences of the rat and porcine luteinizing hormone-human chorionic gonadotropin receptor proteins SEQ ID NO:3 and 4) respectively and the FSH and TSH receptors SEQ ID NO:6 and 5) respectively having similar action. The same amino acid residue as appears in the human luteinizing hormone-human chorionic gonadotropin receptor protein of the present invention, is represented by ".", and an amino acid residue different from that of the human LH/hCG receptor is represented by the appropriate symbol as defined herein. CONSENSUS shown in FIGS. 2A–2D indicates amino acid residues common to all the glycoproteins shown in FIGS. 2A–2D. The illustration of CONSENSUS results in introduction of lacking portions "–" into the formulae ih FIGS. 2A–2D. Accordingly, the number representing the amino acids is counted excluding these lacking portions.

For a DNA sequence, the DNA coding for the human LH/hCG receptor of the present invention contains the nucleotide sequence SEQ ID NO:1 shown in FIGS. 1A–1E or a portion thereof.

As the CDNA coding for the human LH/hCG receptor of the present invention, any CDNA may be used as long as it contains a nucleotide sequence coding for an amino acid sequence of the human LH/hCG receptor. For example, DNA containing the nucleotide sequence SEQ ID NO:1 shown in FIGS. 1A–1E or a portion thereof is preferably used.

The nucleotide sequence SEQ ID NO:1 shown in FIGS. 1A–1E are an example of cDNA sequences coding for the human LH/hCG receptor obtained in the present invention.

In the present invention, for example, an expression vector having the CDNA containing the nucleotide sequence coding for the human LH/hCG receptor can be prepared by the following process:

(a) Messenger RNA (mRNA) is isolated from human LH/hCG receptor-producing cells.

(b) Single stranded complementary DNA (cDNA) is synthesized from the MRNA, followed by synthesis of double stranded DNA.

(c) The complementary DNA is introduced into a phage or a plasmid.

(d) Host cells are transformed with the recombinant phage or plasmid thus obtained.

(e) After cultivation of the transformants thus obtained, plasmids or phages containing the desired DNA are isolated from the transformants by an appropriate method such as hybridization with a DNA probe coding for a portion of the rat LH/hCG receptor or immunoassay using an anti-LH/hCG receptor antibody.

(f) The desired cloned DNA is cut out from the recombinant DNA.

(g) The cloned DNA or a portion thereof is ligated downstream from a promoter in the expression vector.

The mRNA coding for the human LH/hCG receptor can be obtained from various human LH/hCG receptor-producing cells, for example, germ cells such as the Leydig cells in the testis, the capsular cells in the ovary, the granulosa cells, the corpus luteum cells and the interstitial cells.

Methods for preparing the mRNA from the human LH/hCG receptor-producing cells include the guanidine thiocyanate method [J. M. Chirgwin et al., *Biochemistry* 18, 5294 (1979)] and the like.

Using the mRNA thus obtained as a template, cDNA is synthesized by use of reverse transcriptase, for example, in accordance with the method of H. Okayama et al. [*Molecular and Cellular Biology* 2, 161 (1979); and ibid. 3, 280 (1983)]. The cDNA thus obtained is introduced into the plasmid.

The plasmids into which the cDNA may be introduced include, for example, pBR322 [*Gene* 2, 95 (1977)], pBR325 [*Gene* 4, 121 (1978)], pUC12 [*Gene* 19, 259 (1982)) and pUC13 [*Gene* 19, 259, each derived from *Escherichia coli*, and pUB110 derived from *Bacillus subtilis* [*Biochemical and Biophysical Research Communication* 112, 678 (1983)]. However, any other plasmid can be used as long as it is replicable and viable in the host cell. Examples of the phage vectors into which the cDNA may be introduced include λgt11 [R. Young and R. Davis, *Proc. Natl. Acad. Sci. U.S.A.* 80, 1194 (1983)]. However, any other phage vector can be used as long as it is viable in the host cell.

Methods for introducing the cDNA into the plasmid include, for example, the method described in T. Maniatis et al., *Molecular Cloning*, Cold Spring Harbor Laboratory, p.239 (1982). Methods for introducing the cDNA into the phage vector include, for example, the method of T. V. Hyunh et al. [*DNA Cloning, A Practical Approach* 1, 49 (1985)].

The plasmid thus obtained is introduced into an appropriate host cell such as Escherichia and Bacillus.

Examples of Escherichia described above include *E. coli* K12DH1 [*Proc. Natl. Acad. Sci. U.S.A.* 60, 160 (1968)], M103 [*Nucleic Acids Research* 9, 309 (1981)], JA221 [*Journal of Molecular Biology* 120, 517 (1978)], HB101 [*Journal of Molecular Biology* 41, 459 (1969)] and C600 [*Genetics* 39, 440 (1954)].

Examples of Bacillus described above include *Bacillus subtilis* MI114 (*Gene* 24, 255 (1983)] and 207–21 [*Journal of Biochemistry* 95, 87 (1984)].

Methods for transforming the host cell with the plasmid include, for example, the calcium chloride method or the calcium chloride/rubidium chloride method described in T. Maniatis et al., *Molecular Cloning*, Cold Spring harbor Laboratory, p.249 (1982).

When the phage vector is used, for example, it can be transduced into proliferated *E. coli*, using the in vitro packaging method.

Human LH/hCG receptor-cDNA libraries containing human LH/hCG receptor cDNA can be purchased from the market, though obtainable by the methods described above. For example, a cDNA library of the LH/CG receptor is available from Clontech Laboratories, Inc., U.S.A.

Methods for cloning human LH/hCG receptor cDNA from the human DNA library include, for example, the plaque hybridization method using phage vector λcharon 28A and rat LH/hCG receptor cDNA as a probe [T. Maniatis et al., *Molecular Cloning*, Cold Spring Harbor Laboratory, (1982)].

The human LH/hCG receptor cDNA thus cloned may be subcloned, for example, in pBR322, pUC12, pUC13, pUC18, pUC19, pUC118 and pUC119 to obtain the human LH/hCG receptor cDNA, if necessary.

The nucleotide sequence of the cDNA thus obtained is determined, for example, by the Maxam-Gilbert method [A. M. Maxam and W. Gilbert, *Proc. Natl. Acad. Sci. U.S.A.* 74, 560 (1977)] or the dideoxy method [J. Messing et al., *Nucleic Acids Research* 9, 309 (1981)], and the existence of the human LH/hCG receptor cDNA is confirmed in comparison with the known amino acid sequence.

As described above, the cDNA coding for the human LH/hCG receptor protein is obtained.

FIGS. 1A–1E show the nucleotide sequence of the cDNA SEQ ID NO:1 determined by the dideoxy method for the cDNA coding for the human LH/hCG receptor protein obtained in Example 1 described below, and the amino acid sequence proved from that nucleotide sequence.

The CDNA coding for the human LH/hCG receptor protein SEQ ID NO:2 cloned as described above can be used as is, or after digestion with a restriction enzyme if desired, depending on the intended use.

A region intended to be expressed is cut out from the cloned cDNA and ligated downstream from a promoter in a vehicle (vector) suitable for expression, whereby the expression vector can be obtained.

The cDNA has ATG as a translation initiating codon at the 5'-terminus thereof and may have TAA, TGA or TAG as a translation terminating codon at the 3'-terminus. The translation initiating codon and translation terminating codon may be added by use of an appropriate synthetic cDNA adaptor. A promoter is further ligated upstream therefrom for the purpose of expressing the cDNA.

Examples of the vectors include the above plasmids derived from *E. coli* such as pBR322, pBR325, pUC12 and pUC13, the plasmids derived from *Bacillus subtilis* such as pUB110, pTP5 and pC194, plasmids derived from yeast such as pSH19 and pSH15, bacteriophages such as A phage, and animal viruses such as retroviruses and vaccinia viruses.

As the promoter used in the present invention, any promoter is available as long as it is suitable for expression in the host cell selected for the gene expression.

When the host cell used for transformation is Escherichia, it is preferable that a trp promoter, a lac promoter, a recA promoter, a $\lambda P_L$ promoter, a lpp promoter, etc. are used. When the host cell is Bacillus, it is preferable that a SPO1 promoter, a SPO2 promoter, a penP promoter, etc. are used. When the host cell is yeast, it is preferable that a PHO5 promoter, a PGK promoter, a GAP promoter, an ADH promoter, etc. are used. In particular, it is preferable that the host cell is Escherichia and the promoter is the trp promoter or the $\lambda P_L$ promoter.

When the host cell is an animal cell, a SV-40 derived promoter, a retrovirus promoter, a metallothionein promoter, a heat shock promoter, etc. are each usable.

An enhancer is also effectively used for expression.

Using a vector containing the cDNA coding for the mature peptide of the human LH/hCG receptor protein thus constructed, transformants are prepared.

The host cells include, for example, Escherichia, Bacillus, yeast and animal cells.

Specific examples of the above Escherichia and Bacillus include strains similar to those described above.

Examples of the above yeast include *Saccharomyces cerevisiae* AH22, AH22R$^-$, NA87-11A and DKD-5D.

Examples of the animal cells include monkey cell COS-7, Vero, Chinese hamster cell (CHO), mouse L cell and human FL cell.

The transformation of the above Escherichia is carried out, for example, according to the method described in *Proc. Natl. Acad. Sci. U.S.A.* 69, 2110 (1972) or *Gene* 17, 107 (1982).

The transformation of the above Bacillus is conducted, for example, according to the method described in *Molecular & General Genetics* 168, 111 (1979).

The transformation of the yeast is carried out, for example, according to the method described in *Proc. Natl. Acad. Sci. U.S.A.* 75, 1929 (1978).

The transformation of the animal cells is carried out, for example, according to the method described in *Virology* 52, 456 (1973).

Thus, transformants are obtained which have been transformed with the expression vector containing the cDNA coding for the human LH/hCG receptor.

When bacterial transformants are cultured, a liquid medium is particularly suitable as a medium used for culture. Carbon sources, nitrogen sources, inorganic compounds and others necessary for growth of the transformants are contained therein. Examples of the carbon sources include glucose, dextrin, soluble starch and sucrose. Examples of the nitrogen sources include inorganic or organic materials such as ammonium salts, nitrates, corn steep liquor, peptone, casein, meat extracts, soybean meal and potato extract solution. The inorganic compounds include, for example, calcium chloride, sodium dihydrogenphosphate and magnesium chloride. Yeast, vitamins, growth promoting factors and so on may be further added thereto.

The pH of the medium is preferably about 5 to 8.

As the medium used for cultivation of Escherichia, for example, M9 medium containing glucose and Casamino Acids (Miller, *Journal of Experiments in Molecular Genetics* 431–433, Cold Spring Harbor Laboratory, New York, 1972) is preferably used. In order to make the promoter act efficiently, a drug such as 3-β-indolylacrylic acid may be added thereto if necessary.

When the host cell is Escherichia, the cultivation is usually carried out at about 15 to 43° C. for about 3 to 24 hours, with aeration or agitation if necessary.

When the host cell is Bacillus, the cultivation is usually carried out at about 30 to 40° C. for about 6 to 24 hours, with aeration or agitation if necessary.

When yeast transformants are cultured, for example, Burkholder minimum medium [K. L. Bostian et al., *Proc. Natl. Acad. Sci. U.S.A.* 77, 4505 (1980)] is used as the medium. The pH of the medium is preferably adjusted to about 5 to 8. The cultivation is usually carried out at about 20 to 35° C. for about 24 to 72 hours, with aeration or agitation if necessary.

When animal cell transformants are cultured, examples of the mediums include MEM medium containing about 5 to 20% fetal calf serum [*Science* 122, 501 (1952)], DMEM medium [*Virology* 8, 396 (1959)], RPMI1640 medium (*The Journal of the American Medical Association* 199, 519 (1967)] and 199 medium [*Proceeding of the Society for the Biological Medicine* 73, 1 (1950). The pH is preferably about 6 to 8. The cultivation is usually carried out at about 30 to 40° C. for about 15 to 60 hours, with aeration or agitation if necessary.

The human LH/hCG receptor protein can be isolated and purified from the culture described above, for example, by the following method.

When the human LH/hCG receptor protein is extracted from the cultured cells, the cells are collected by methods known in the art after cultivation. Then, the collected cells are suspended in an appropriate buffer solution and disrupted by ultrasonic treatment, lysozyme and/or freeze-thawing. Thereafter, a crude extracted solution of the human LH/hCG receptor mature peptide is obtained by centrifugation or filtration. The buffer solution may contain a protein denaturant such as urea or guanidine hydrochloride, or a surface-active agent such as Triton X-100.

When the human LH/hCG receptor protein is secreted in the culture solution, a supernatant is separated from the cells by methods known in the art after the conclusion of cultivation, and then collected.

The separation and purification of the human LH/hCG receptor contained in the culture supernatant or the extracted solution thus obtained can be performed by an appropriate combination of known separating and purifying methods. The known separating and purifying methods include methods utilizing solubility such as salt precipitation and solvent precipitation, methods mainly utilizing a difference in molecular weight such as dialysis, ultrafiltration, gel filtration and SDS-polyacrylamide gel electrophoresis, methods utilizing a difference in electric charge such as ion-exchange column chromatography, methods utilizing specific affinity such as affinity chromatography, methods utilizing a difference in hydrophobicity such as reverse phase high performance liquid chromatography and methods utilizing a difference in isoelectric point such as isoelectro-focussing electrophoresis. A method may also be used in which an antibody to a fused protein expressed by fusing the human LH/hCG receptor complimentary DNA together with *E. coli*-derived DNA lacZ is used as an immunoaffinity column.

The activity of the human LH/hCG receptor protein thus formed can be measured by an enzyme immunoassay using a specific antibody.

The cells transfected or transformed with the cDNA of the present invention can allow the human LH/hCG receptor protein to be produced in large amounts.

The human LH/hCG receptor protein produced here is channeled into the study of ovarian physiology, the supply of antibodies to the receptor, the diagnosis and management of ovarian or testicular diseases such as ovulation aberration or oligospermia, and the development of contraceptives. In humans, this TSH receptor can be a target of autoimmune reaction which leads to hyper- or hypo-stimulation of the thyroid gland by autoantibodies in Grave's disease and idiopathic myxedema. The LH/hCG receptor might therefore suppress the LH action in vivo or can conduct hyperstimulation in stead of LH to cause morbidity in the human genital system. The anti-receptor antibody can be detected by producing the receptor by any of the above-described methods, labeling it and examining whether one binding to it (antibody) is present in vivo or not. In addition, it is considered that inhibition of the LH action by an antibody obtained by expressing a portion or all of the receptor cDNA, namely the application of the antibody as a contraceptive, is possible.

There have been described above in detail the cloning of the cDNA coding for the human LH/hCG receptor protein, the preparation of the expression vectors for the human LH/hCG receptor protein, the production of the transformants thereby, the production of the human LH/hCG receptor protein by using the transformants and utility thereof.

When nucleotides, amino acids and so on are indicated by abbreviations in this specification and drawings, the abbreviations adopted by the IUPAC-IUB Commission on Biochemical Nomenclature or commonly used in the art are employed. For example, the following abbreviations are used. When the amino acids are capable of existing as optical isomers, it is understood that the L-forms are represented unless otherwise specified.

DNA: Deoxyribonucleic acid

CDNA: Complementary deoxyribonucleic acid

A: Adenine

T: Thymine

G: Guanine

C: Cytosine

RNA: Ribonucleic acid mRNA: Messenger ribonucleic acid dATP: Deoxyadenosine triphosphate dTTP: Deoxythymidine triphosphate dGTP: Deoxyguanosine triphosphate dCTP: Deoxycytidine triphosphate ATP: Adenosine triphosphate EDTA: Ethylenediaminetetraacetic acid SDS: Sodium dodecyl sulfate Gly or G: Glycine Ala or A: Alanine Val or V: Valine Leu or L: Leucine Ile or I: Isoleucine Ser or S: Serine Thr or T: Threonine Cys or C: Cysteine Met or M: Methionine Glu or E: Glutamic acid Asp or D: Aspartic acid Lys or K: Lysine Arg or R: Arginine His or H: Histidine Phe or F: Phenylalanine Tyr or Y: Tyrosine Trp or W: Tryptophan Pro or P: Proline Asn or N: Asparagine Gln or Q: Glutamine The precise chemical structure of the human luteinizing hormone-human chorionic gonadotropin receptor proteins of the present invention will depend on a number of factors. Because ionizable amino and carboxyl groups are present in these proteins, a particular protein may be obtained as an acidic or basic salt, or in neutral form. All such preparations which retain their bioactivity when placed in suitable environmental conditions are included in the definition of the receptor proteins of the present invention. Further, the primary amino acid sequence of such proteins may be argumented by derivation using sugar moieties or by other supplementary molecules such as lipids, phosphate, acetyl groups and the like. Such modifications are included in the definition of the receptor proteins of the present invention so long as the bioactivity of the protein is not destroyed. It is expected, of course, that such modifications may quantitatively or qualitatively affect the bioactivity by either enhancing or diminishing the activity of the protein.

Further, individual amino acid residues in the chain may be modified by oxidation, reduction, or other derivatization, and the receptor proteins of the present invention may be cleaved to obtain fragments which retain bioactivity. Such alterations which do not destroy bioactivity do not remove such receptor proteins from the definition.

Finally modifications to the primary structure itself by deletion, addition, or alteration of the amino acids incorporated into the sequence during translation can be Mmade without destroying the activity of the receptor proteins of the present invention.

The present invention will hereinafter be described in more detail with the following Examples. It is understood of course that these Examples are not intended to limit the scope of the invention.

Transformant *E. coli* JM109/pUC18 obtained in Example 1 described below was deposited with the Fermentation Research Institute, the Agency of Industrial Science and Technology, the Ministry of International Trade and Industry, Japan (FRI) under the accession number FERM BP-3127 on Oct. 9, 1990. This microorganism was deposited with the Institute for Fermentation, Osaka, Japan (IFO) under the accession number IFO 15096 on Oct. 11, 1990.

Transformants *E. coli* DH1/pHLHR (UEX2) and *E. coli* JM109/pHLHR (GEX-3X) obtained in Example 2 described below were deposited with the Fermentation Research Institute, the Agency of Industrial Science and Technology, the Ministry of International Trade and Industry, Japan (FRI) under the accession number FERM BP-3545 and FERM BP-3544 respectively on Aug. 29, 1991. These transformants were deposited with the Institute For Fermentation, Osaka, Japan (IFO) under the accession numbers IFO 15219 on Aug. 30, 1991 and IFO 15218 on Aug. 30, 1991, respectively.

EXAMPLE 1

(1) Preparation of a Human Ovary-Derived cDNA Library

Total RNA was extracted from the human ovary by the guanidine thiocyanate method, and then mRNA was purified by use of an oligo(dt) cellulose column (Type 7, Pharmacia). Using a cDNA synthesizing kit (Pharmacia), cDNA was synthesized from about 2 μg of purified mRNA. The terminus of this cDNA was rendered flush with T4 DNA polymerase, followed by addition of an EcoRI adapter. This cDNA was bound to a λgt10 vector, and in vitro packaging was carried out by use of a packaging kit (Gigapack Gold, Stratagene). This library contained $1\times10^6$ independent recombinants, and was proliferated.

(2) Purification of a Probe

A cDNA library was prepared from the rat ovary in a manner similar to that described above, and inserted into a λZaPII vector (Stratagene). A rat LH/hCG receptor was cloned therefrom to isolate clones Zap3-5-1 (2.8 kb). The clones were labeled using the random primer method (Amersham), and used as a probe.

(3) Screening

A λgt10 cDNA library phage solution of $5\times10^4$ plaque forming units (pfu) was mixed with 500 μl of C600hfl (cultivated overnight), and the mixture was incubated at 37° C. for 15 minutes. Then, 8 ml of 0.75% agarose (Nippon Gene) LB was added thereto, and the mixture was inoculated on a 1.5% agar LB plate (15 cm dish). A nitrocellulose filter (Hybond-N, Amersham) was placed on the plate on which plaques were formed, and DNA was fixed. Subsequently, the filter was prehybridized at 65° C. for 1 to 2 hours in a solution prepared by adding 0.1% bovine serum albumin (BSA), polyvinylpyrrolidone, Ficoll 400 (Pharmacia), 5% pyrophosphoric acid and 0.1% SDS to 6×SSC (0.15 M NaCl, 0.015 M sodium citrate, pH 7.0). On hybridization, the probe was added to 200,000 cpm/ml as a guide. The filter was washed with 6×SSC at 42° C. for 15 minutes, and subsequently with 0.1×SSC at 65° C. for 10 minutes. Then, the filter was subjected to autoradiography at −70° C.

(4) Analysis of DNA Sequence

Some clones were identified, and the longest was selected from these clones for sequence analysis. This clone was subcloned into pUC18 (Takara), and *E. coli* JM109 was transformed with the resulting plasmid to yield transformant *E. coli* JM109/pUC18 (FERM BP-3127). This transformant was further shaved off stepwise by exonuclease digestion to prepare long to short single stranded DNA fragments. Sequence analysis was carried out by the dideoxy chain terminal method using a 7DEAZA sequencing kit. Electrophoresis was carried out by use of a LKB2010 Macrophor sequencing system. The SDC Genetyx software was used for data analysis.

FIGS. 1A–1E show the nucleotide sequence SEQ ID NO:1 of the DNA of the human LH/hCG receptor protein, as well as the amino acid sequence deduced therefrom. The nucleotide sequence obtained in the present invention has additional 8 DNAs (−8 to −1) prior to N-terminus of the nucleotide sequence of SEQ ID NO:1.

EXAMPLE 2

Expression of Human LH/HCG Receptor Protein (Sometimes Referred to Herein as HLHR Protein)

(1) The HLHR cDNA clones obtained in Example 1 were used. The lac Z-HLHR fusion gene was obtained by cloning the 1400 bp EcoRI-Xba fragment coding for extracellular segment of the HLHR into the BamHI site of pUEX2. The lac Z-HLHR fusion construction was transformed into *E. coli* DH1 host to yield transformant *E. coli* DH1/pHLHR (UEX2) (FERM BP-3545).

For preparation of lacZ-HLHR fusion protein, the transformant was cultivated in LB overnight at 30° C. 5 ml of the LB medium was innoculated with 50 μl of the overnight culture. After incubation of 2 hr at 30° C. with aeration and further incubation of 2 hr at 42° C., the cells were pelleted.

The pellets were dissolved in a SDS-polyacrylamide gel electrophoresis (PAGE) sample buffer. The solution was subjected to 5% SDS-PAGE. *E. coli* transformed with pUEX2 vector was similarlly subjected to 5% SDS-PAGE. After electrophoresis, the gel was stained with Coomassie Blue. The result is shown in FIG. 3. Lane 1 shows a molecular weight marker, lane 2 shows the case of pUEX2 vector and lane 3 shows the present transformant. A band at 110 kda of lane 2 disappears and a new band at 159 kda appears. The result of the electrophoresis and analysis of the nucleotide sequence show the expression of HLHR protein.

(2) The GST (glutathion S-transferase) –HLHR fusion gene was obtained by cloning the 1400 bp EcoRI-Xba fragment coding for extracellular segment of the HLHR into the BamHI site of pGEX-3X(Pharmacia). The GST-HLHR fusion construction was transformed into *E. coli* JM 109 host to yield *E. coli* JM109/pHLHR(GEX-3X) (FERM BP-3544). The transformant was cultivated in LB overnight at 30° C. The overnight culture of JM 109 was diluted 1:10 in 500 ml of fresh medium and cultivated for 1 hr at 37° C. before adding IPTG to 0.1 mM. After further 7 hr culture, the cells were pelleted.

Figure 4:
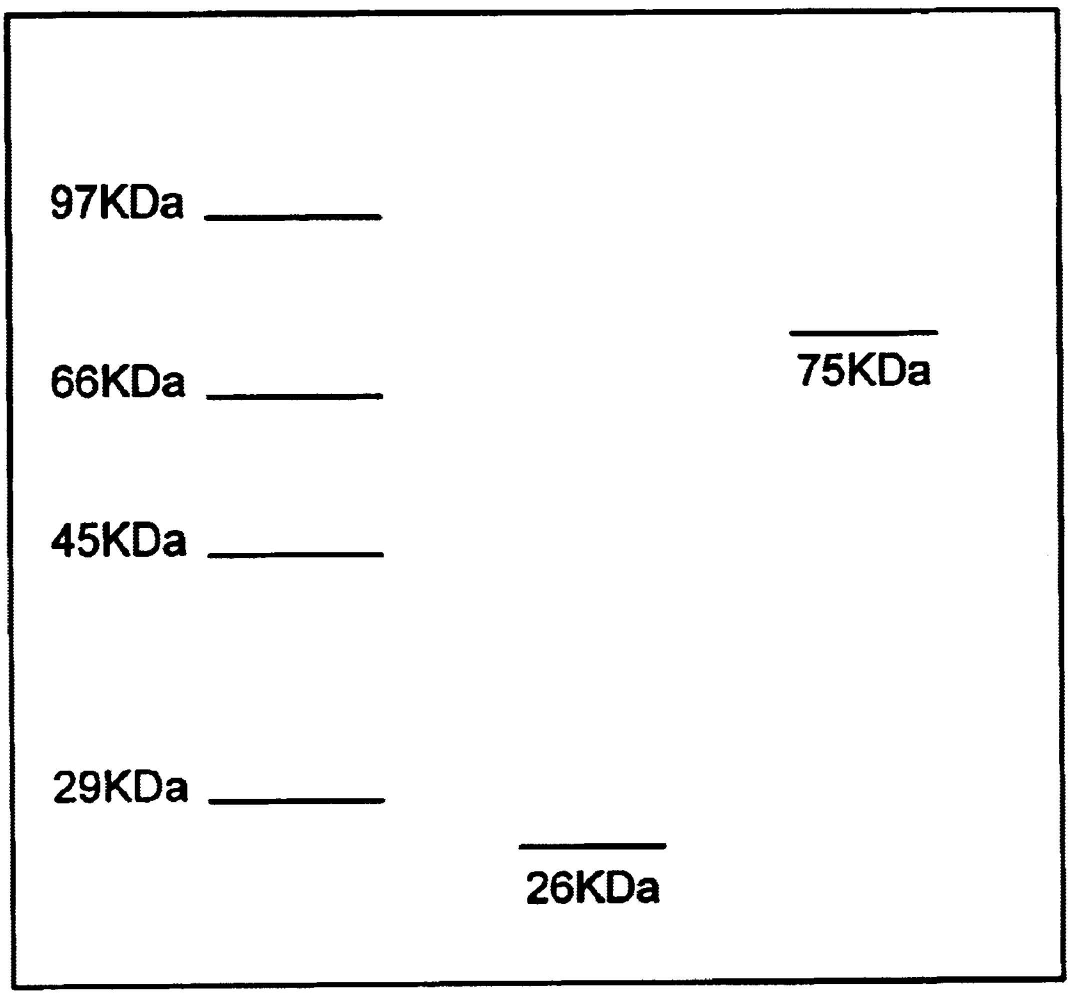

The pellets were dissolved in a SDS-polyacrylamide gel electrophoresis (PAGE) sample buffer. The solution was subjected to 10% SDS-PAGE. *E. coli* transformed with pGEX-3X vector was similarily subjected to 10% SDS-PAGE. After electrophoresis, the gel was stained with Coomassie Blue. The result is shown in FIG. 4. Lane 1 shows a molecular weight marker, lane 2 shows the case of pGEX-3X vector and lane 3 shows the present transformant. A band at 26 kda of lane 2 disappears and a new band at 75 kda appears. The result of the electrophoresis and analysis of the nucleotide sequence show the expression of HLHR protein.

(3) Functional Expression of HLHR

Figure 5:
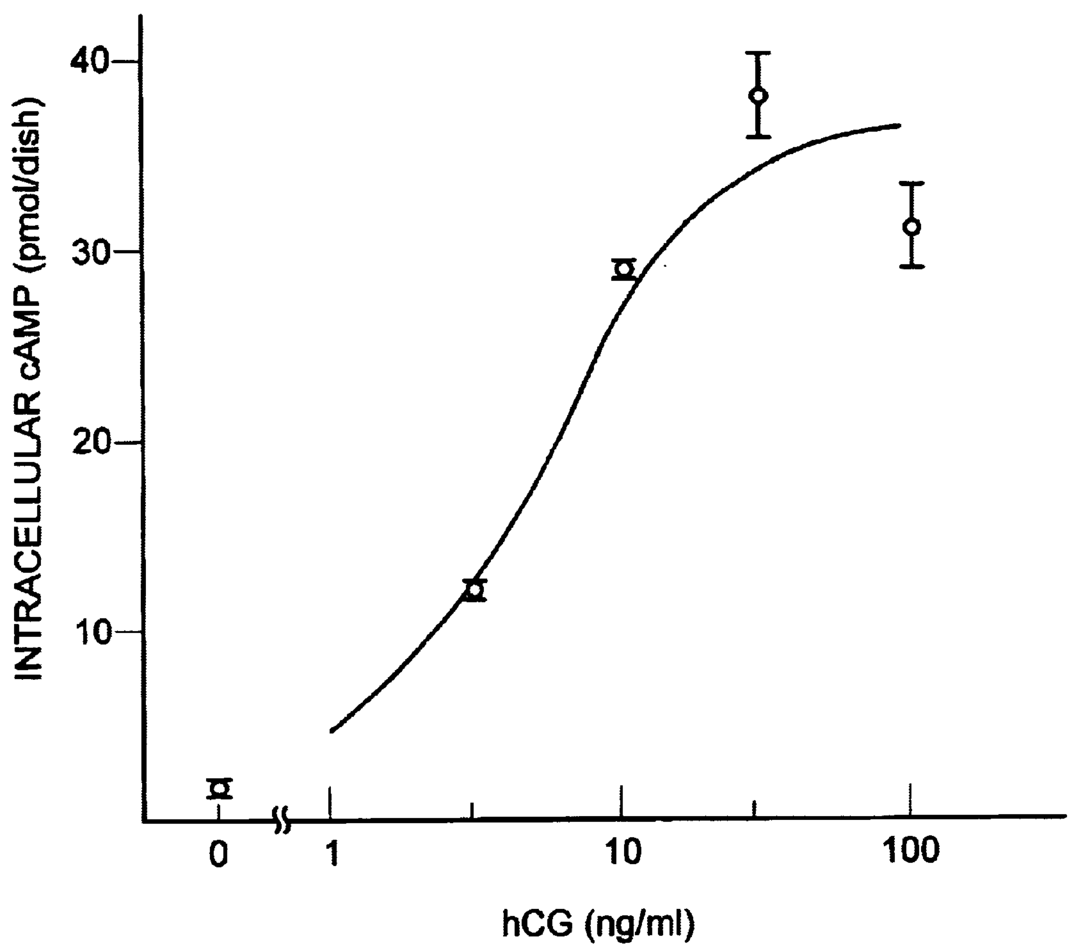
FIG. 5 is a graph which shows that the protein obtained according to the present invention has response ability to hCG.

The expression vector PCHLHR was constructed by introducing the entire coding region of the cloned cDNA and additional flunking regions contained on an RcoRI fragment (2995 bp) into the pCDNA 1 vector. Human kidney 293 cells (ATCC CRL 1573) were maintained in Dulbecco's modified Eagle's medium containing 10% Fetal Calf serum in a humidified atmosphere containing 5% $CO_2$. These cells were transiently transfected with pCHLHR, an expression vector encoding for the full-length human LH/hCG receptor, according to the procedure of calcium phosphate-mediated transfection. These cells were tested for their response ability to hCG with an increase in cAMP levels. The result is shown in FIG. 5. In FIG. 5, the points indicate the mean and the bars indicate the range of the data.

The present invention has been described in detail, including the preferred embodiments thereof. However, it will be appreciated that those skilled in the art, upon consideration of the present disclosure, may make modifications and improvements on this invention and still be within the scope and spirit of this invention as set forth in the following claims.

What is claimed is:

1. An isolated DNA coding for a human luteinizing hormone-chorionic gonadotropin receptor protein in which said protein has an amino acid sequence represented by SEQ ID NO:2.

2. The isolated DNA claimed in claim 1, wherein said DNA has a nucleotide sequence represented by the $1^{st}$ to $2987^{th}$ nucleotides of SEQ ID NO:1.

3. The isolated DNA claimed in claim 1, wherein said DNA has a nucleotidie sequence represented by SEQ ID NO:14, a nucleotide sequence represented by the $1^{st}$ to $2097^{th}$ nucleotides of SEQ ID NO:1.

4. The isolated DNA claimed in claim 1, wherein said DNA has a nucleotide sequence represented by SEQ ID NO:12, a nucleotide sequence represented by the $76^{th}$ to $2987^{th}$ nucleotides of SEQ ID NO:1.

5. The isolated DNA claimed in claim 1, wherein said DNA has a nucleotide sequence represented by SEQ ID NO:15, a nucleotide sequence rcpresented by the $76^{th}$ to $2097^{th}$ nucleotides of SEQ ID NO:1.

6. A host cell carrying the DNA sequence of claim 1.

7. A method for producing a human lutcinizing hormone-human chorionic gonadotropin receptor protein which comprises cultivating a transformant carrying a DNA according to claim 1, accumulating the protein encoded by the DNA in a culture broth and collecting the protein.

* * * * *